(12) United States Patent
Goldin et al.

(10) Patent No.: US 7,041,448 B2
(45) Date of Patent: May 9, 2006

(54) GENE ENCODING A NEW TRP CHANNEL IS MUTATED IN MUCOLIPIDOSIS IV

(75) Inventors: Ehud Goldin, Rockville, MD (US); Susan A. Slaugenhaupt, Quincy, MA (US); Mei Sun, Rockville, MD (US); James S. Acierno, Jr., Quincy, MA (US)

(73) Assignees: The ML4 Foundation, Brooklyn, NY (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 09/851,494

(22) Filed: May 8, 2001

(65) Prior Publication Data

US 2003/0064363 A1  Apr. 3, 2003

Related U.S. Application Data

(60) Provisional application No. 60/226,388, filed on Aug. 18, 2000.

(51) Int. Cl.
*C12Q 1/68* (2006.01)
*C12N 15/12* (2006.01)

(52) U.S. Cl. ............... 435/6; 435/69.1; 435/252.3; 435/320.1; 536/23.5; 536/24.31

(58) Field of Classification Search .............. 435/69.1, 435/252.3, 320.1; 530/350; 536/23.5
See application file for complete search history.

(56) References Cited

U.S. PATENT DOCUMENTS 6,300,096 B1  10/2001  Stahl et al.
2002/0035056 A1*  3/2002  Curtis et al.
2002/0182671 A1*  12/2002  Lal et al.

FOREIGN PATENT DOCUMENTS

WO   WO-WO 01/77331 A1   10/2001

OTHER PUBLICATIONS

Sun et al. "Mucolipidosis type IV is caused by mutations in a gene encoding a novel transient receptor potential channel." Human Molecular Genetics vol. 9(17):2471-2478, Sep. 2000.*

Bargal et al. "Identification of the gene causing mucolipidosis type IV." Nature Genetics vol. 26:120-123, Sep. 2000.*

Bassi et al. "Cloning of the gene encoding a novel integral membrane protein, Mucolipidin-and identification of the two major founder mutations causing mucolipidosis type IV." American Journal of Human Genetics vol. 67:1110-1120, 2000.*

"From Worm To Man: Three Subfamilies of TRP Channels", Christian Harteneck et al., Trends Neurosci., vol. 23, No. 4, 2000, Elsevier Science Ltd., 2000.

"Compromised Cytoarchitecture and Polarized Trafficking in Autosomal Dominant Polycystic Kidney Disease Cells", Audra J. Charron et al., The Journal of Cell Biology, vol. 149, No. 1, Apr. 3, 2000, The Rockefeller University Press.

"Cellular and Subcellular Distribution of Polycystin-2, the Protein Product of the PKD2 Gene", Lukas Foggensteiner et al., Journal of the American Society of Nephrology, 2000.

"Ion Channels and Synaptic Organization: Analysis of the Drosophila Genome", J. Troy Littleton et al., Neuron, vol. 26, 35-43, Apr. 2000, Cell Press 2000.

"Mucolipidosis IV Consists of One Complementation Group", EHUD Goldin et al., Proc. Natl. Acad. Sci., USA, vol. 96, pp. 8562-8566, Jul. 1999, Genetics.

"Mapping of the Mucolipidosis Type IV Gene to Chromosome 19p and Definition of Founder Haplotypes.", Susan A. Slaugenhaupt et al., The American Society of Human Genetics, 1999.

"Mucolipidosis Type IV Characteristic MRI Findings", Dr. K.P. Frei et al., American Academy of Neurology, 1998.

"Abnormal Transport Along the Lysosomal Pathway in Mucolipidosis, Type IV Disease", Chii-Shiarng Chen et al., Proc. Natl. Acad. Sci., USA, vol. 95, pp 6373-6378, May 1998, Medical Sciences.

(Continued)

*Primary Examiner*—John Ulm
(74) *Attorney, Agent, or Firm*—Darby & Darby

(57) ABSTRACT

The present invention relates to identification of a gene that is inactivated in a mucolipidosis condition. In particular, the invention concerns mutations that disrupt a mucolipin, preferably MCOLN1, in mucolipidosis IV. Recombinant nucleic acids encoding mutant forms of MCOLN1, oligonucleotides specific for such mutations, and diagnostic and therapeutic applications related to these discoveries, are also contemplated.

46 Claims, 6 Drawing Sheets

OTHER PUBLICATIONS

"Constitutive Achlorhydria in Mucolipidosis Type IV", Raphael Schiffmann et al., Proc. Natl. Acad. Sci., USA, vol. 95, pp 1207-1212, Feb. 1998, Medical Sciences.

"Recommendations for a Nomenclature System for Human Gen Mutations", Dr. Stylianos E. Antonarakis et al., Human Mutation 11:1-3 (1998), Wiley-Liss, Inc. 1998.

"Cultured Skin Fibroblasts Derived From Patients With Mucolipidosis 4 Are Auto-Fluorescent", Ehud Goldin et al., Pediatric Research, vol. 37, No. 6, 1995, International Pediatric Research Foundation, Inc. 1995.

"The Effect of Lysosomal Storage Diseases on Secretory Cells: An Ultrastructural Study of Pancreas as an Example", I. Hammel et al.; J. Submicrosc. Cytol., Pathology, 27 (2), 143-160, 1995.

"'G' to 'A' Mutation at Position -1 of a 5' Splice Site in a Late Infantile Form of Tay-Sachs Disease", Said Akli et al., The Journal of Biological Chemistry, vol. 265, No. 13, Issue of May 5, pp. 7324-7330, 1990, The American Society For Biochemistry and Molecular Biology, Inc. 1990.

* cited by examiner

GENE ENCODING A NEW TRP CHANNEL IS MUTATED IN MUCOLIPIDOSIS IV

The research leading to this invention was supported, in part, by the U.S. Department of Energy (contract no. W-7405-ENG-48) and The National Institute of Neurological Disease and Stroke (Grant No. NS39945).

This application claims the benefit of the filing date of U.S. Provisional Patent Application No. 60/226,388, filed Aug. 18, 2000 under 35 U.S.C. § 119(e). This prior application is incorporated herein by reference in its entirety.

FIELD OF THE INVENTION

The present invention relates to identification of a protein that is rendered non-functional in a mucolipidosis condition. In particular, the invention concerns mutations that disrupt a TRP channel in Type IV mucolipidosis (MLIV). Recombinant nucleic acids encoding mutant forms of the TRP channel, oligonucleotides specific for such mutations, and diagnostic and therapeutic applications related to these discoveries, are also contemplated.

BACKGROUND OF THE INVENTION

Mucolipidosis type IV (MLIV; MIM 252650) is an autosomal recessive developmental disorder with abnormal brain, eye and gastric functions. It was first described by Berman et al. (J. Pediat. 1974, 84:519–26) who studied an Ashkenazi Jewish infant with corneal clouding, a variety of storage bodies and large vacuoles in many different cell types, in the presence of normal levels of lysosomal hydrolases. The lack of identification of a specific storage compound led to the mucolipidosis classification.

Clinically, MLIV is characterized by a variable degree of growth and psychomotor retardation that is apparent as early as the first year of life. Most patients are unable to speak or walk independently and remain developmentally at a 1–2 year level. Patient head MRI at the time of diagnosis shows a dysplastic corpus callosum and dysmyelinating white matter abnormalities indicating early onset of brain pathology, while cerebellar atrophy is seen predominantly in older patients (Frei et al., Neurology 1998, 51:565–9). MLIV is further characterized by corneal clouding and a progressive retinopathy with optic atrophy, which results in severe visual impairment (Reidel et al., Am. J. Ophthalmol. 1985, 99:125–36). The majority of MLIV patients appear to have a static encephalopathy and do not deteriorate neurologically; however, some patients show a decline in motor function in the second or third decade of life. A simple approach to the diagnosis of MLIV was obtained when we discovered that all patients have constitutive achlorhydria associated with a secondary elevation of serum gastrin levels (Schiffman et al., Proc. Natl. Acad. Sci. 1998, 95:1207–12). At the present time, MLIV is the only genetic disease known to be associated with elevated gastrin.

The gene that is mutated in MLIV, MCOLN1 has been mapped to a 5.6 cM region on chromosome 19p13.2–13.3 by linkage analysis in 26 Ashkenazi Jewish (AJ) families (Slaugenhaupt et al., Am. J. Human Genet. 1999, 65:773–8). In addition, the ethnic bias seen in MLIV is apparently due to a founder effect, with two common haplotypes representing 96% of the chromosomes. Utilizing the finding that the storage bodies in MLIV fibroblasts are autofluorescent (Goldin et al., Pediat. Res. 1995, 37:687–92), a single gene defect in both AJ and non-Jewish (NJ) patients (Goldin et al., Proc. Natl. Acad. Sci. 1999, 96:8562–6), was implicated by complementation assays. However, there remained a need to identify a specific gene involved in this disease.

SUMMARY OF THE INVENTION

The present invention represents a significant step forward in understanding and treating mucolipidosis. By identifying a specific protein that is rendered non-functional in people suffering from one form of mucolipidosis, MLIV, the tools for studying the molecular biology of mucolipidosis are made available. Furthermore, identification of this protein, and the genetic polymorphisms or variations that lead to its functional inactivation, provides strategies for overcoming these defects. These strategies can be used broadly to affect any mucolipidosis, particularly mucolipidosis IV.

Thus, in a first embodiment, the invention provides a nucleic acid (SEQ ID NOS: 1 and 2) encoding MCOLN1 (SEQ ID NO:3); the MCOLN1 protein is also called "mucolipin". In particular, the invention provides an isolated MCOLN1 gene (this gene had previously been referred to as MCL4) including non-coding and non-transcribed sequences. The invention also provides a MCOLN1 cDNA, i.e., free of introns.

In another embodiment, the invention provides mutant MUL4 neucleic acids and MCOLN1 proteins.

In still another embodiment, the invention provides methods for detecting a genetic mutation associated with MLIV comprising detecting a polymorphism or variation in a gene for MCOLN1 which results in a defect in expression of the functional MCOLN1. In a further embodiment, the invention provides a method for diagnosing a mucolipidos or an ion channel defect comprising detecting such a mutation. In a specific embodiment, the invention provides a method for predicting the likelihood of developing mucolipidosis or an ion channel defect, and particularly for genetic counseling of prospective parents.

In yet another embodiment, the invention provides a kit for detecting a mutation in the gene encoding MCOLN1 which results in a defect in expression of functional MCOLN1, using an oligonucleotide that specifically hybridizes to the site of the mutation or to an adjacent site on the gene.

Still another embodiment of the invention provides vectors that express functional human MCOLN1 in human target cells and a method of treating a mucolipidosis associated with such a defect by administering the vector into cells (such as bone marrow cells) of the subject. Pharmaceutical compositions comprising the vector are also provided.

In yet another embodiment, the invention provides a method of screening for candidate compounds that modulate activity of MCOLN1, by detecting binding of MCOLN1 with a compound and isolating the compound.

Another embodiment of the invention provides a kit comprising a MCOLN1 polypeptide and a binding detector that indicates MCOLN1 binding with a compound for screening for a candidate compound that modulates the activity of MCOLN1.

These and other embodiments of the invention are described in greater detail in the accompanying drawings, Detailed Description, and Examples.

DESCRIPTION OF THE DRAWING

FIGS. 2A, 2B, 2C and 2D. Expression of MCOLN1 and mutation detection in AJ MLIV. Lanes in a–c correspond to the following: 1, parent heterozygous for the major AJ haplotype; 2, patient homozygous for the major AJ haplotype ; 3, non-carrier sibling of the patient; 4, patient heterozygous for the major and minor AJ haplotypes; 5, parent heterozygous for the minor AJ haplotype; 6, patient homozygous for the minor AJ haplotype; 7, non-carrier sibling of the patient; 8, AJ patient from family 20 heterozygous for the major and a unique haplotype; 9, AJ patient from family 18 heterozygous for the minor and a unique haplotype. (A) Northern analysis of MCOLN1 mRNA from fibroblasts in AJ MLIV patients and family members showing a significant reduction of the message in patients carrying the major and minor haplotypes. (B) Analysis of the major AJ mutation in MCOLN1. The major AJ mutation, g.5534A>G, introduces a KpnI restriction site. A 541-bp fragment was amplified from genomic DNA and digested in patients homozygous for the major haplotype resulting in two fragments of 344-bp and 197-bp (lane 2), carriers and patients heterozygous for the major haplotype have the 541, 344, and 197-bp bands (lanes 1 and 8), and normal controls show only the 541-bp band (lanes 3 and 7). A patient homozygous for the minor haplotype shows no product (lane 6). (C) Analysis of the minor AJ mutation in MCOLN1. A forward primer at bp 226 of the MCOLN1 genomic sequence (AF287270) and a reverse primer at the end of exon 7 amplify a 377-bp fragment in carriers and patients of the minor haplotype (lanes 4, 5, 6, and 9). The longer 6.8-kb normal fragment is not amplified in this reaction. (D) Northern analysis of MCOLN1 in NJ and AJ patients. Fibroblasts samples: lane 1, normal control; 2, family 48; 3, family 41; 4, family 50; 5, family 42; 6, family 53. MCOLN1 mRNA is expressed in all patients except for family 50. Lymphoblast samples: lane 7, family 53; 8, family 20; 9, family 44; 10, normal control; 11, patient homozygous for the major AJ mutation; 12, patient heterozygous for the major and minor AJ mutation; 13, patient homozygous for the minor AJ haplotype; 14, normal control. MCOLN1 mRNA shows lower expression in lymphoblasts in both normal and patient samples.

FIGS. 4A and 4B. Alignment of MCOLN1 with related proteins. (A) Alignment of mucolipin (SEQ ID NO:3) to human BAA91951* (SEQ ID NO:4), which includes the alternatively spliced exon 3, and AAF49118, which is Drosophila CG8743 (SEQ ID NO: 5). Putative transmembrane domains (thick lines) and the TRPL motif domain (thin line) are indicated. (B) Predicted hydrophobicity plot of mucolipin compared to aa 170–750 of human PKD2 indicating structural similarity. Putative transmembrane domains are indicated.

DETAILED DESCRIPTION OF THE INVENTION

Figure 1A:
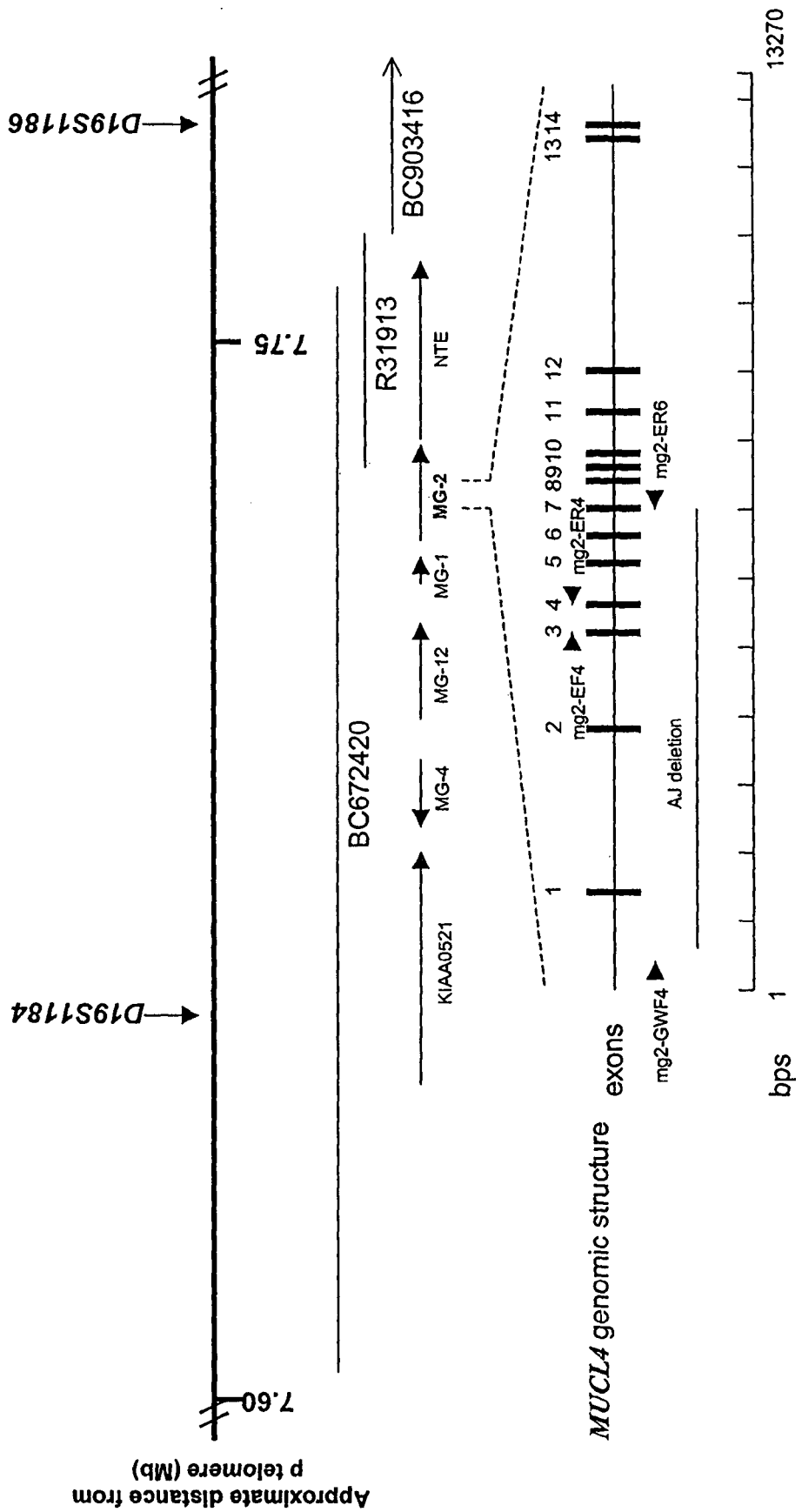
FIGS. 1A, and 1B. Physical maps of the MCOLN1 candidate region. (A) Shows the closest flanking markers, D19S1184 and D19S1186. Genes that map within the candidate region are shown with the arrow designating transcription orientation. The schematic diagram depicts the genomic structure of the MCOLN1 gene. Primers used for amplification of the major AJ mutation (mg2-EF4 and mg2-ER4) and the minor AJ deletion mutant (mg2-GWF4 and mg2-ER6) are shown. The base pair scale corresponds to the MCOLN1 genomic sequence entry AF287270 (SEQ ID NO:1), and the extent of the AJ deletion is shown. (B) Physical map and transcript map of the MCOLN1 region on chromosome 19p. PCR-based localization of markers (in italics) and of GeneMap '99 ESTs (boxed, with known gene names in boldface italics immediately after the corresponding EST) is shown above the overlapping BAC map. D19S216 is located 2.95 cM telomeric to D19S869, and D19S413 is located 6.02 cM centromeric to D19S922 (markers not shown on map). An asterisk denotes markers identified for this study. The 143-kb region between D19S1184 and D19S1886 and known to contain MCOLN1 is shown on the transcript map at the bottom. Genes are depicted with arrows to represent transcriptional orientation. The Alu bar depicts the 27 kb of repetitive sequence.

Mucolipidosis Type IV is a developmental neurodegenerative disorder characterized by severe neurologic and ophthalmologic abnormalities. The MLIV gene, MCOLN1, has recently been localized to chromosome 19p13.2–13.3 by genetic linkage. The present invention involves the cloning of this novel transient receptor potential cation channel gene and the demonstration that this gene is mutated in patients with the disorder. MCOLN1 encodes a protein, mucolipin, that has six predicted transmembrane domains and is a member of the polycystin II subfamily of the Drosophila TRP gene family. Receptor-stimulated cation channel defect thus appears to play a role in the pathogenesis of mucolipidosis IV.

The present invention is based, in part, on additional 9 AJ and 5 NJ families that were studied in addition to the studies reported in Slaugenhaupt et al. (Am. J. Human Genet. 1999, 65:777–8). We conducted a detailed haplotype analysis in order to pinpoint the gene location and determine the probable number of mutations. There are 5 unique haplotypes in the AJ population. The major and minor haplotypes are present on 73% and 23% of chromosomes, respectively. The remaining three haplotypes were only seen once; in two cases coupled with the major and once with the minor haplotype. Analysis of the 5 NJ families yielded an additional 7 unique haplotypes, suggesting that there may be as many as 12 independent mutations. Linkage disequilibrium analysis of the 2 common haplotypes enabled us to narrow the candidate region to 143 kb and we constructed a detailed transcript map of this interval.

The present invention advantageously provides oligonucleotides specific for mutations of the gene encoding MCOLN1, including both probes for directly detecting mutated sequences and PCR primers for amplifying sites where such mutations are found to occur.

Furthermore, MCOLN1, including mutant forms of MCOLN1, can be expressed in eukaryotic and prokaryotic cells and can be used to develop and/or implement high throughput screens to identify novel agonists and antagonists of MCOLN1 activity, such as channel function.

The term "functional MCOLN1" refers to an MCOLN1 that functions in a cell, e.g., plays a role as a TRP channel or a receptor-stimulated cation channel. Evidence of MCOLN1 function can be detected by various methods. MCOLN1 functions include, but are not limited to, HCl secretion, ion channel activity, and secretion of solutes from intracellular vesicles. Other MCOLN1 functions include, but are not limited to, binding with MCOLN1-specific antibodies.

A "defect in expression of functional MCOLN1" refers to an alteration in the sequence of a genomic MCOLN1 gene (also termed herein a "mutation") that causes failure of expression of MCOLN1 or that causes expression of an MCOLN1 protein or polypeptide that is non-functional.

Preferably such non-functionality is reflected in cellular defects that manifest as mucolipidosis. A non-functional MCOLN1 protein or polypeptide is termed herein a "mutant MCOLN1 protein".

MLIV is a disease with phenotypic characteristics similar to mucopolysaccharidosis without sugar in the urine, with features that include growth and mental retardation, corneal clouding and lysosomal inclusions. MLIV is in the category of channelopathies, i.e., ion channel defects. Thus, the present invention concerns mucolipidosis and certain other conditions that result from an ion channel defect, wherein the ion channel is MCOLN1.

In a specific embodiment, the term "about" or "approximately" means within 20%, preferably within 10%, and more preferably within 5% of a given value or range.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

The use of italics indicates a nucleic acid molecule (e.g., MCOLN1, refers to a cDNA, gene, etc.); normal text indicates the polypeptide or protein.

Cloning and Expression of MCOLN1

The present invention contemplates analysis and isolation of a nucleic acid encoding a functional or mutant MCOLN1, including a full length, or naturally occurring form of MCOLN1, and any antigenic fragments thereof from any human source. It further contemplates expression of functional or mutant MCOLN1 protein for evaluation, diagnosis, or therapy.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Molecular Biology—Definitions

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

"Chemical sequencing" of DNA denotes methods such as that of Maxam and Gilbert (Maxam-Gilbert sequencing, Maxam and Gilbert, Proc. Natl. Acad. Sci. USA 1977 74:560), in which DNA is randomly cleaved using individual base-specific reactions.

"Enzymatic sequencing" of DNA denotes methods such as that of Sanger (Sanger et al., Proc. Natl. Acad. Sci. USA 1977, 74:5463), in which a single-stranded DNA is copied and randomly terminated using DNA polymerase, including variations thereof well-known in the art.

The term "single-strand conformational polymorphism analysis" (SSCP) refers to a method for detecting sequence differences between two DNAs, comprising hybridization of the two species with subsequent mismatch detection by gel electrophoresis (Ravnik-Glavac et al., Hum. Mol. Genet. 1994, 3:801)

"HOT cleavage" is defined herein as a method for detecting sequence differences between two DNAs, comprising hybridization of the two species with subsequent mismatch detection by chemical cleavage (Cotton, et al., Proc. Natl. Acad. Sci. USA 1988, 85:4397).

"Denaturing gradient gel electrophoresis" (DDGE) refers to a method for resolving two DNA fragments of identical length on the basis of sequence differences as small as a single base pair change, using electrophoresis through a gel containing varying concentrations of denaturant (Guldberg et al., Nuc. Acids Res. 1994, 22:880.)

As used herein, "sequence-specific oligonucleotides" refers to related sets of oligonucleotides that can be used to detect allelic variations or mutations (polymorphisms) in the MCOLN1 gene.

A "probe" refers to a nucleic acid or oligonucleotide that forms a hybrid structure with a sequence in a target region due to complementarity of at least one sequence in the probe with a sequence in the target protein.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In a specific embodiment, the term "gene" refers to the gene as found in the chromosome, including non-coding sequences (introns and 5' and 3' untranslated sequences) and non-transcribed sequences (such as the promoter and any other transcriptional control sequence), such as an enhancer or repressor sequence).

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of" or "operatively associated with" transcriptional and translational control sequences in a cell when RNA polymerase transcribes the coding sequence into mRNA, which is then trans-RNA spliced (if it contains introns) and translated into the protein encoded by the coding sequence.

The term "host cell" means any cell or any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell, such as a transmembrane or membrane-associated protein. A substance is "secreted" by a cell if it appears in significant measure outside the cell, from somewhere on or inside the cell.

The term "transfection" means the introduction of a heterologous nucleic acid into a cell. The term "transformation" or "transduction" means the introduction of a heterologous gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, heterologous DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, and insect host cells and *Baculovirus* vectors.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, an MCOLN1 gene is heterologous to the vector DNA in which it is inserted for cloning or expression, and it is heterologous to a host cell containing such a vector, in which it is expressed, e.g., a CHO cell.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95%) of the nucleotides match over the defined length of the DNA sequences, as determined by sequence comparison algorithms, such as BLAST, FASTA, DNA Strider, etc. An example of such a sequence is an allelic or species variant of the specific MCOLN1 genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of MCOLN1, or to detect the presence of nucleic acids encoding MCOLN1. In a further embodiment, an oligonucleotide of the invention can form a triple helix with a MCOLN1 DNA molecule. In still another embodiment, a library of oligonucleotides arranged on a solid support, such as a silicon wafer or chip, can be used to detect various polymorphisms of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of MCOLN1 of the invention. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule. etc.).

MCOLN1 Nucleic Acids

A gene encoding MCOLN1, whether genomic DNA or cDNA, can be isolated from any source, particularly from a human cDNA or genomic library. Methods for obtaining MCOLN1 gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein (e.g., a neural, corneal, gastric, muscle, spleen, kidney, liver, or placenta cell library, since these are the cells that evidence levels of expression of MCOLN1), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Identification of the specific DNA fragment containing the desired MCOLN1 gene may be accomplished in a number of ways. For example, a portion of a MCOLN1 gene exemplified infra can be purified and labeled to prepare a labeled probe, and the generated DNA may be screened by nucleic acid hybridization to the labeled probe (Benton and Davis, Science 196:180, 1977; Grunstein and Hogness, Proc. Natl. Acad. Sci. U.S.A. 72:3961, 1975). Those DNA fragments with substantial homology to the probe, such as an allelic variant from another individual, will hybridize. In a specific embodiment, highest stringency hybridization conditions are used to identify a homologous MCOLN1 gene.

In a specific embodiment, the invention provides a genomic sequence of the MCOLN1 gene (SEQ ID NO:1). It also provides a CDNA sequence (SEQ ID NO: 2). The nucleic acids of the invention include an additional 186 amino acid N-terminal coding sequence relative to XP_008934 (NCBI).

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of MCOLN1 protein as disclosed herein. Thus, the presence of the gene may be detected by assays based on the physical, chemical, immunological, or functional properties of its expressed product.

The present invention also relates to cloning vectors containing genes encoding analogs and derivatives of MCOLN1 of the invention, that have the same or homologous functional activity as MCOLN1. The production and use of derivatives related to MCOLN1, including MCOLN1 mutants, are within the scope of the present invention. For example, a truncated form of MCOLN1 can be provided. Such a truncated form includes MCOLN1 with a deletion. In a specific embodiment, the derivative is functionally active, i.e., capable of exhibiting one or more functional activities associated with a full-length, wild-type MCOLN1 of the invention. Such functions include mRNA translation into protein (i.e., ribosome function).

MCOLN1 derivatives can be made by altering encoding nucleic acid sequences by substitutions, additions or deletions that provide for functionally similar molecules, i.e., molecules that perform one or more MCOLN1 functions. Alternatively, non-functional or less functional mutant forms of MCOLN1, that may for example transport or secret vesicular contents less effectively than wild type, can be prepared as discussed above. Sequence variants can be created to introduce or eliminate restriction in enzyme cleavage sites. In a specific embodiment, infra, the mutation is selected from the following Table:

TABLE 1

MCOLN1 Mutations

| Haplotype | Nucleotide change | Mutation type | Amino acid change |
|---|---|---|---|
| AJ major | g.5534A>G | splice | — |
| AJ minor | g.511-6944del | 6434-bp genomic del | — |

TABLE 1-continued

MCOLN1 Mutations

| Haplotype | Nucleotide change | Mutation type | Amino acid change |
|---|---|---|---|
| 18 (AJ) | g.511-6944del | 6434-bp genomic del | — |
|  | c.1334-1335insT | frameshift* | — |
| 20 (AJ) | g.5534A>G | splice | — |
|  | c.1346-1348delCTT | aa del | F408del |
| 44 (AJ) | g.5534A>G | splice | — |
|  | unknown |  |  |
| 48 (NJ) | g.9107A>G$^a$ | splice | 454-469del |
| 41 (NJ) | c.1461G>T | aa substitution | V446L |
| 42 (NJ) | c.429C>T | nonsense | R102X |
|  | c.1209G>T | aa substitution | D362T |
| 50 (NJ) | g.511-6944del | 6434-bp genomic del | — |
|  | c.598-599delCC | frameshift* | — |
| 53 (NJ) | c.639C>T | nonsense | R172X |
|  | g.9107A>G$^a$ | splice | — | g. mutations denoted using genomic sequence (AF287270),
c. mutation denoted using cDNA sequence (AF287269),
*translational frameshift mutations that result in termination codons,
$^a$bp substitution creates a new preferred splice acceptor site that results in the deletion of 15 AA. (Nomenclature according to Antonarkis, Hum. Mutat. 198, 11:1–3)

Other DNA sequences which encode substantially the same amino acid sequence as a MCOLN1 gene may be used in the practice of the present invention. These include but are not limited to allelic variants, species variants, sequence conservative variants, and functional variants, e.g., NCB1 XP$_{13}$ 008934.

Amino acid substitutions may also be introduced to substitute an amino acid with a particularly preferable property. For example, a Cys may be introduced a potential site for disulfide bridges with another Cys.

The genes encoding MCOLN1 derivatives and analogs of the invention can be produced by various methods known in the art. The manipulations which result in their production can occur at the gene or protein level. For example, the cloned MCOLN1 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of MCOLN1, care should be taken to ensure that the modified gene remains within the same translational reading frame as the MCOLN1 gene, uninterrupted by translational stop signals, in the gene region where the desired activity is encoded.

Additionally, the MCOLN1-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Such modifications can be made to introduce restriction sites and facilitate cloning the MCOLN1 gene into an expression vector. Any technique for mutagenesis known in the art can be used, including but not limited to, in vitro site-directed mutagenesis (Hutchinson, C., et al., J. Biol. Chem. 253:6551, 1978; Zoller and Smith, DNA 3:479–488, 1984; Oliphant et al., Gene 44:177, 1986; Hutchinson et al., Proc. Natl. Acad. Sci. U.S.A. 83:710, 1986), use of TAB" linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2m plasmid.

Expression of MCOLN1 Polgpeptides

The nucleotide sequence coding for MCOLN1, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, a nucleic acid encoding MCOLN1 of the invention can be operationally associated with a promoter in an expression vector of the invention. Both cDNA and genomic sequences can be cloned and expressed under control of such regulatory sequences. Such vectors can be used to express functional or functionally inactivated MCOLN1 polypeptides. As used herein, an "MCOLN1 polypeptide" refers to all or a portion of MCOLN1. The portion of MCOLN1 preferably binds to a binding partner of MCOLN1, such as a MCOLN1-specific antibody, or a small molecule modulator of MCOLN1.

The necessary transcriptional and translational signals can be provided on a recombinant expression vector, or they may be supplied by the native gene encoding MCOLN1 and/or its flanking regions.

Potential host-vector systems include but are not limited to mammalian cell systems infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In particular, yeast expression systems can also be used according to the invention to express MCOLN1. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Expression of MCOLN1 protein may be controlled by any promoter/enhancer element known in the art, but these regulatory elements must be functional in the host selected for expression. Promoters which may be used to control MCOLN1 gene expression include, but are not limited to, cytomegalovirus (CMV) promoter, the SV40 early promoter region (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296:39–42, 1982); prokaryotic expression vectors such as the β-lactamase promoter (Villa-Komaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, and alkaline phosphatase promoter.

Vectors

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31–40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Preferred vectors are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant MCOLN1 protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo, ex vivo or in vitro targeting and therapy procedures are DNA-based vectors and retroviral vectors. Methods for constructing and using viral vectors are known in the art (see, e.g., Miller and Rosman, BioTechniques 1992, 7:980–990). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991, 2:320–330), defective herpes virus vector lacking a glyco-protein L gene (Patent Publication RD 371005 A), or other defective herpes virus vectors (PCT Publication Nos. WO 94/21807 and WO 92/05263); an attenuated adenovirus vector, such as the vector described by Stratford-Perricaudet et al. (J. Clin. Invest. 1992 90:626–630; see also La Salle et al., Science 1993, 259:988–990); and a defective adeno-associated virus vector (Samulski et al., J. Virol. 1987 61:3096–3101; Samulski et al., J. Virol. 1989, 63:3822–3828; Lebkowski et al., Mol. Cell. Biol. 1988, 8:3988–3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-g (IFN-g), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Adenovirus vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1–L5.

In a specific embodiment, the adenoviral vector has a deletion in the E1 region (Ad 1.0). Examples of E1-deleted adenoviruses are disclosed in EP 185,573, the contents of which are incorporated herein by reference. In another embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., Gene 101:195 1991; EP 185 573; Graham, EMBO J. 3:2917, 1984). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36:59 1977) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987) 1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are manipulated to destroy the viral packaging signal, but retain the structural genes required to package the co-introduced virus engineered to contain the heterologous gene and the packaging signals. Thus, the viral particles that are produced are not capable of producing additional virus.

Lentivirus vectors. In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest. For a review, see, Naldini, Curr. Opin. Biotechnol., 9:457–63, 1998.

Lentiviruses contain at least two regulatory genes, tat and rev, that are essential for replication, and four accessory genes that encode critical virulence factors. The viral sequences non-essential for transduction are eliminated, thereby improving the biosafety of this particular vector. Self-inactivating HIV-1 vectors are known, which have a deletion in the 3' long terminal repeat (LTR) including the TATA box, and significantly improve the biosafety of HIV-derived vectors by reducing the likelihood that replication-competent retroviruses will originate in the vector producer and target cells (Zufferey, et al., J. Virol., 72:9873–80, 1998). In addition, the deletion improves the potential performance of the vector by removing LTR sequences previously associated with transcriptional interference and suppression in vivo and by allowing the construction of more-stringent tissue-specific or regulatable vectors.

Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virusparticles at titers greater than 106 IU/ml for at least 3 to 4 days (Kafri, et al., J. Virol., 73: 576–584, 1999). The vector produced by the inducible cell line can be concentrated as needed for efficiently transducing nondividing cells in vitro and in vivo.

Non-viral vectors. In one embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A. 84:7413–7417, 1987; Felgner and Ringold, Science 337: 387–388, 1989; see Mackey, et al., Proc. Natl. Acad. Sci. U.S.A. 85:8027–8031, 1988; Ulmer et al., Science 259: 1745–1748, 1993). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Naked DNA vectors can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 267:963–967, 1992; Wu and Wu, J. Biol. Chem. 263: 14621–14624, 1988; Hartmut et al., Canadian Patent Application No. 2,012,311, filed Mar. 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S. Pat. Nos. 5,580, 859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci. 1998, 321:893; WO 99/01157; WO 99/01158; WO 99/01175).

Antibodies to MCOLN1

Antibodies to MCOLN1 are useful, inter alia, for diagnostics and intracellcular regulation of MCOLN1 activity, as set forth below. According to the invention, MCOLN1 polypeptides produced recombinantly or by chemical synthesis, and fragments or other derivatives or analogs thereof, including fusion proteins, may be used as an immunogen to generate antibodies that recognize the MCOLN1 polypeptide. Such antibodies include but are not limited to polyclonal, monoclonal, chimeric, single chain, Fab fragments, and an Fab expression library. Such an antibody is specific for human MCOLN1; it may recognize a mutant form of MCOLN1, or wild-type MCOLN1.

Various procedures known in the art may be used for the production of polyclonal antibodies to MCOLN1 polypeptide or derivative or analog thereof. For the production of antibody, various host animals can be immunized by injection with the MCOLN1 polypeptide, or a derivative (e.g., fragment or fusion protein) thereof, including but not limited to rabbits, mice, rats, sheep, goats, etc. In one embodiment, the MCOLN1 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the MCOLN1 polypeptide, or fragment, analog, or derivative thereof, any technique that provides for the production of antibody molecules by continuous cell lines in culture may be used. These include but are not limited to the hybridoma technique originally developed by Kohler and Milstein (Nature 1975, 256:495–497), as well as the trioma technique, the human B-cell hybridoma technique (Kozbor et al., Immunology Today 198, 4:72; Cote et al., Proc. Natl. Acad. Sci. USA 1983 80:2026–2030), and the EBV-hybridoma technique to produce human monoclonal antibodies (Cole et al., in Monoclonal Antibodies and Cancer Therapy, Alan R. Liss, Inc. 1985, pp. 77–96). In an additional embodiment of the invention, monoclonal antibodies can be produced in germ-free animals (PCT Publication No. WO 89/12690). In fact, according to the invention, techniques developed for the production of "chimeric antibodies" (Morrison et al., J. Bacteriol. 1984, 159:870); Neuberger et al., Nature 1984, 312:604–608; Takeda et al., Nature 1985, 314:452–454) by splicing the genes from a mouse antibody molecule specific for an MCOLN1 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

According to the invention, techniques described for the production of single chain antibodies (U.S. Pat. Nos. 5,476,786 and 5,132,405 to Huston; U.S. Pat. No. 4,946,778) can be adapted to produce MCOLN1 polypeptide-specific single chain antibodies. An additional embodiment of the invention utilizes the techniques described for the construction of Fab expression libraries (Huse et al., Science 1989, 246:1275–1281) to allow rapid and easy identification of monoclonal Fab fragments with the desired specificity for an MCOLN1 polypeptide, or its derivatives, or analogs.

In the production and use of antibodies, screening for or testing with the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an MCOLN1 polypeptide, one may assay generated hybridomas for a product which binds to an MCOLN1 polypeptide fragment containing such epitope. For selection of an antibody specific to an MCOLN1 polypeptide from a particular species of animal, one can select on the basis of positive binding with MCOLN1 polypeptide expressed by or isolated from cells of that species of animal.

The foregoing antibodies can be used in methods known in the art relating to the localization and activity of the MCOLN1 polypeptide, e.g., for Western blotting, imaging MCOLN1 polypeptide in situ, measuring levels thereof in appropriate physiological samples, etc. using any of the detection techniques mentioned above or known in the art. Such antibodies can also be used in assays for ligand binding, e.g., as described in U.S. Pat. No. 5,679,582.

In a specific embodiment, antibodies that agonize or antagonize the activity of MCOLN1 polypeptide can be generated. In particular, intracellular single chain FV antibodies can be used to regulate (inhibit) MCOLN1. Such antibodies can be tested using the assays described infra for identifying ligands.

Screening and Chemistry

According to the present invention, nucleotide sequences derived from the gene encoding a polymorphic form of a MCOLN1, and peptide sequences derived from that polymorphic form of MCOLN1, are useful targets to identify drugs that are effective in treating aplastic, hypoplastic, or hyperproliferative disorders. Drug targets include without limitation (i) isolated nucleic acids derived from the gene encoding a MCOLN1 and (ii) isolated peptides and polypeptides derived from MCOLN1 polypeptides, each of which may comprise one or more polymorphic positions.

In particular, identification and isolation of MCOLN1 provides for development of screening assays, particularly for high throughput screening of molecules that up- or down-regulate the activity of MCOLN1, e.g., by permitting expression of MCOLN1 in quantities greater than can be isolated from natural sources, or in indicator cells that are specially engineered to indicate the activity of MCOLN1 expressed after transfection or transformation of the cells. Accordingly, the present invention contemplates methods for identifying specific ligands of MCOLN1 using various screening assays known in the art.

Any screening technique known in the art can be used to screen for MCOLN1 agonists or antagonists. The present invention contemplates screens for small molecule ligands or ligand analogs and mimics, as well as screens for natural ligands that bind to and agonize or antagonize activates MCOLN1 in vivo. For example, natural products libraries can be screened using assays of the invention for molecules that agonize or antagonize MCOLN1 activity.

Knowledge of the primary sequence of the, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 1990, 249:386–390; Cwirla, et al., Proc. Natl. Acad. Sci. 1990, 87:6378–6382; Devlin et al., Science 1990, 49:404–406), very large libraries can be constructed ($10^6$–$10^8$ chemical entities). A second approach uses primarily chemical methods, of which the Geysen method (Geysen et al., Molecular Immunology 1986, 23:709–715; Geysen et al. J. Immunologic Method 1987,102:259–274; and the method of Fodor et al. (Science 1991, 251:767–773) are examples. Furka et al. (14th International Congress of Biochemistry, Volume #5, Abstract FR:013, 1988; Furka, Int. J. Peptide Protein 1991, Res. 37:487–493), Houghton (U.S. Pat. No. 4,631,211 and Rutter et al. (U.S. Pat. No.

5,010,175) describe methods to produce a mixture of peptides that can be tested as agonists or antagonists.

In another aspect, synthetic libraries (Needels et al., Proc. Natl. Acad. Sci. USA 1993, 90:10700–4; Ohlmeyer et al., Proc. Natl. Acad. Sci. USA 1993, 90:10922–10926; Lam et al., PCT Publication No. WO 92/00252; Kocis et al., PCT Publication No. WO 94/28028) and the like can be used to screen for MCOLN1 ligands according to the present invention.

Test compounds are screened from large libraries of synthetic or natural compounds. Numerous means are currently used for random and directed synthesis of saceharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., Tib Tech, 14:60, 1996).

In Vitro Screening Methods

In one series of embodiments, an isolated nucleic acid comprising one or more polymorphic positions is tested in vitro for its ability to bind test compounds in a sequence-specific manner. The methods comprise:

(i) providing a first nucleic acid containing a particular sequence at a polymorphic position and a second nucleic acid whose sequence is identical to that of the first nucleic acid except for a different sequence at the same polymorphic position;

(ii) contacting the nucleic acids with a multiplicity of test compounds under conditions appropriate for binding; and (iii) identifying those compounds that bind selectively to either the first or second nucleic acid sequence.

Selective binding as used herein refers to any measurable difference in any parameter of binding, such as, e.g., binding affinity, binding capacity, etc.

In another series of embodiments, an isolated peptide or polypeptide comprising one or more polymorphic positions is tested in vitro for its ability to bind test compounds in a sequence-specific manner. The screening methods involve:

(i) providing a first peptide or polypeptide containing a particular sequence at a polymorphic position and a second peptide or polypeptide whose sequence is identical to the first peptide or polypeptide except for a different sequence at the same polymorphic position;

(ii) contacting the polypeptides with a multiplicity of test compounds under conditions appropriate for binding; and (iii) identifying those compounds that bind selectively to one of the nucleic acid sequences.

In preferred embodiments, high-throughput screening protocols are used to survey a large number of test compounds for their ability to bind the genes or peptides disclosed above in a sequence-specific manner.

In vivo Screening Methods

Intact cells or whole animals expressing polymorphic variants of a gene encoding MCOLN1 can be used in screening methods to identify candidate drugs.

In one series of embodiments, a permanent cell line is established from an individual exhibiting a particular polymorphic pattern. Alternatively, cells (including without limitation mammalian, insect, yeast, or bacterial cells) are programmed to express a gene comprising one or more polymorphic sequences by introduction of appropriate DNA. Identification of candidate compounds can be achieved using any suitable assay, including without limitation (i) assays that measure selective binding of test compounds to particular polymorphic variants of MCOLN1 (ii) assays that measure the ability of a test compound to modify (i.e., inhibit or enhance) a measurable activity or function of MCOLN1 and (iii) assays that measure the ability of a compound to modify (i.e., inhibit or enhance) the transcriptional activity of sequences derived from the promoter (i.e., regulatory) regions the MCOLN1 gene.

MCOLN1 knockout mammals can be prepared for evaluating the molecular pathology of this defect in greater detail than is possible with human subjects. Such animals also provide excellent models for screening drug candidates. A "knockout mammal" is an mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild-type allele) and a homozygous mutant (i.e., two defective alleles). Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Pfeffer et al. (Cell 1993, 73:457–467) describe mice in which the gene encoding the tumor necrosis factor receptor p55 has been suppressed. Fung-Leung et al. (Cell 1991, 65:443–449; J. Exp. Med. 1994, 174:1425–1429) describe knockout mice lacking expression of the gene encoding CD8.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene.

By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

Generally, the DNA will be at least about 1 kilobase (kb) in length and preferably 3–4 kb in length, thereby providing sufficient complementary sequence for hybridization when the knockout construct is introduced into the genomic DNA of the ES cell (discussed below).

Included within the scope of this invention is a mammal in which two or more genes have been knocked out. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. Nos. 4,959,317 and 5,801,030).

In another series of embodiments, transgenic animals are created in which (i) a human MCOLN1 having different sequences at particular polymorphic positions are stably inserted into the genome of the transgenic animal; and/or (ii) the endogenous MCOLN1 genes are inactivated and replaced with human MCOLN1 genes having different sequences at particular polymorphic positions see, e.g., Coffman, Semin. Nephrol. 1997, 17:404; Esther et al., Lab. Invest. 1996, 74:953; Murakami et al., Blood Press. Suppl. 1996, 2:36. Such animals can be treated with candidate compounds and monitored for anemia.

Furthermore, populations that are not amenable to an established treatment for aplastic, hypoplastic, or hyperproliferative disorders can be selected for testing of alternative treatments. Moreover, treatments that are not as effective in the general population, but that are highly effective in the selected population, may be identified that otherwise would be overlooked. This is an especially powerful advantage of the present invention, since it eliminates some of the randomness associated with clinical trials.

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time. Such high-throughput screening methods are particularly preferred. The use of high-throughput screening assays to test for agents is greatly facilitated by the availability of large amounts of purified polypeptides, as provided by the invention.

Screening Kits

The components required to practice the screening methods described above can be prepared in kit form, for the convenience of the user. Such kits are preferably adapted for use in an automated screening apparatus.

Methods of Diagnosis

A According to the present invention, genetic variants of MCOLN1 can be detected to diagnose a mucolipidosis, especially MLIV. They can also be used to diagnose subjects evidencing symptoms of MLIV. Various methods for detecting such variants are described herein. Where such variants impact MCOLN1 function, either as a result of a mutated amino acid sequence or because the mutation results in expression of a truncated protein, reduced levels of protein express, or no expression at all, they are expected to result in symptoms of mucolipidosis. In specific embodiment, a MCOLN1 mutation results in MLIV.

More importantly, the invention permits genetic counseling of prospective parents and in vitro genetic testing for a mucolipidosis condition. The methods of the present invention can also be used to predict the predisposition of an individual to develop a symptom of mucolipidosis.

By providing the genomic gene and DNA sequences for MCOLN1, the invention permits detection of any polymorphism, and correlation of that polymorphism with a mucolipidsosis symptom or condition. The invention advantageously provides two major mutations that will permit widespread genetic counseling and screening: AJ major (genomic sequence 5534A G, which results in a splice mutation) and AJ minor (genomic sequence deletion of bases 511 to 6944, resulting in a 6434 bp genomic deletion). Those and other specific mutations are listed in Table 1.

TABLE 1

| MCOLN1 Mutations | | | |
|---|---|---|---|
| Haplotype | Nucleotide change | Mutation type | Amino acid change |
| AJ major | g.5534A>G | splice | — |
| AJ minor | g.511-6944del | 6434-bp genomic del | — |
| 18 (AJ) | g.511-6944del | 6434-bp genomic del | — |
|  | c.1334-1335insT | frameshift* | — |
| 20 (AJ) | g.5534A>G | splice | — |
|  | c.1346-1348delCTT | aa del | F408del |
| 44 (AJ) | g.5534A>G | splice | — |
|  | unknown |  |  |
| 48 (NJ) | g.9107A>G$^a$ | splice | 454-469del |
| 41 (NJ) | c.1461G>T | aa substitution | V446L |
| 42 (NJ) | c.429C>T | nonsense | R102X |
|  | c.1209G>T | aa substitution | D362Y |
| 50 (NJ) | g.511-6944del | 6434-bp genomic del | — |
|  | c.598-599delCC | frameshift* | — |
| 53 (NJ) | c.639C>T | nonsense | R172X |
|  | g.9107A>G$^a$ | splice | — | g. mutations denoted using genomic sequence (AF287270),
c. mutation denoted using cDNA sequence (AF287269),
*translational frameshift mutations that result in termination codons,
$^a$bp substitution creates a new preferred splice acceptor site that results in the deletion of 15 AA. (Nomenclature according Antonarkis Hum. Mutat. 1998, 11:1–3)

A "sample" as used herein refers to a biological sample, such as, for example, tissue (or cells) or fluid isolated from an individual or from in vitro cell culture constituents, as well as samples obtained from the environment or laboratory procedures.

Nucleic Acid Assays

The DNA may be obtained from any cell source. Non-limiting examples of cell sources available in clinical practice include without limitation blood cells, buccal cells, cervicovaginal cells, epithelial cells from urine, fetal cells, or any cells present in tissue obtained by biopsy. Cells may also be obtained from body fluids, including without limitation blood, plasma, serum, lymph, milk, cerebrospinal fluid, saliva, sweat, urine, feces, and tissue exudates (e.g., pus) at a site of infection or inflammation. For prenatal testing, genetic mateiral can be obtained from fetal cells, e.g. from amniotic fluid, (through amniocentesis), chronic villi, blood, or any tissue of a pregnant woman. DNA is extracted using any of the numerous methods that are standard in the art. It will be understood that the particular method used to extract DNA will depend on the nature of the source. Generally, the minimum amount of DNA to be extracted for use in the present invention is about 25 pg (corresponding to about 5 cell equivalents of a genome size of $4 \times 10^9$ base pairs). Sequencing methods are described in detail, supra.

In another alternate embodiment, RNA is isolated from biopsy tissue using standard methods well known to those of ordinary skill in the art such as guanidium thiocyanate-phenol-chloroform extraction (Chomocyznski et al., Anal. Biochem., 162:156, 1987). The isolated RNA is then subjected to coupled reverse transcription and amplification by polymerase chain reaction (RT-PCR), using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, cDNA obtained from the RNA can be cloned and sequenced to identify a mutation.

Protein Assays

In an alternate embodiment, biopsy tissue or cells is obtained from a subject. Antibodies that are capable of distinguishing between different polymorphic forms of MCOLN1 are then contacted with samples of the tissue to determine the presence or absence of a MCOLN1 polypeptide specified by the antibody. The antibodies may be polyclonal or monoclonal, preferably monoclonal. Measurement of specific antibody binding to cells may be accomplished by any known method, e.g., quantitative flow cytometry, or enzyme-linked or fluorescence-linked immunoassay.

Kits

The present invention further provides kits for the determination of the sequence within the MCOLN1 gene in an individual. The kits comprise a means for determining the sequence at the variant positions, and may optionally include data for analysis of mutations. The means for sequence determination may comprise suitable nucleic acid-based and immunological reagents. Preferably, the kits also comprise suitable buffers, control reagents where appropriate, and directions for determining the sequence at a polymorphic position.

Nucleic Acid Based Diagnostic Kits

The invention provides nucleic acid-based methods for detecting genetic variations of MCOLN1 in a biological sample. The sequence at particular positions in the MCOLN1 gene is determined using any suitable means known in the art, including without limitation one or more of hybridization with specific probes PCR amplification, restriction fragmentation, direct sequencing, SSCP, and other techniques known in the art.

The present invention also provides kits suitable for nucleic acid-based diagnostic applications. In one embodiment, diagnostic kits include the following components:

(i) Probe DNA: The probe DNA may be pre-labeled; alternatively, the probe DNA may be unlabeled and the ingredients for labeling may be included in the kit in separate containers; and (ii) Hybridization reagents: The kit may also contain other suitably packaged reagents and materials needed for the particular hybridization protocol, including solid-phase matrices, if applicable, and standards.

In another embodiment, diagnostic kits include:

(i) Sequence determination primers: Sequencing primers may be pre-labeled or may contain an affinity purification or attachment moiety; and (ii) Sequence determination reagents: The kit may also contain other suitably packaged reagents and materials needed for the particular sequencing protocol. In one preferred embodiment, the kit comprises a panel of sequencing primers, whose sequences correspond to sequences adjacent to variant positions.

Antibody Based Diagnostic Kits

The invention also provides antibody-based methods for detecting mutant (or wild type) MCOLN1 proteins in a biological sample. The methods comprise the steps of: (i) contacting a sample with one or more antibody preparations, wherein each of the antibody preparations is specific for mutant (or wild type) MCOLN1 under conditions in which a stable antigen-antibody complex can form between the antibody and MCOLN1 in the sample; and (ii) detecting any antigen-antibody complex formed in step (i) using any suitable means known in the art, wherein the detection of a complex indicates the presence of mutant (or wild type) MCOLN1.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

The present invention also provides kits suitable for antibody-based diagnostic applications. Diagnostic kits typically include one or more of the following components:

(i) MCOLN1-specific antibodies: The antibodies may be pre-labeled; alternatively, the antibody may be unlabeled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Therapeutic Procedures

As noted above, the present invention contemplates various strategies for treatment of diseases or disorders associated with a defect in the expression of a functional MCOLN1 gene, e.g., a mucolipidosis.

Preferably, a subject in whom such treatment is desired will be a human. However, it is possible to use the teachings herein to treat similar diseases in any animal, particularly any mammal.

In all gene therapy cases discussed below, it will be desirable to regulate expression of the therapeutic gene, e.g., by a transient delivery system (such as an adenovirus or naked DNA vector), use of a tissue specific promoter, or use of a regulated expression system (e.g., the tet-regulated expression system; see U.S. Pat. Nos. 5,814,618 and 5,859,310).

Therapeutic compositions of the invention are preferably prepared by an admixture of the active component (e.g., a vector or anti-sense nucleic acid) and a pharmaceutically acceptable carrier or excipient. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

In general, a treatment of mucolipidosis involves transferring a vector comprising a gene for a functional MCOLN1 into target cells of a subject suffering from mucolipidosis, i.e., cells in which MCOLN1 expression has been observed, and in which MCOLN1 mutations results in defects. These include neuronal and gastric cells. The gene transfer techniques and vectors described above are particularly suited for this sort of gene therapy. It is also preferred that the MCOLN1 coding sequence is operatively associated with a promoter that permits high level expression in human cells.

While delivery of an MCOLN1 gene therapy is particularly useful for treatment of MLIV, it is further contemplated that augmenting MCOLN1 activity will benefit subjects suffering from other forms of mucolipidosis. Thus, the therapeutic aspects of this invention are broader than the treatment of MLIV.

To be effective, enough MCOLN1 vector must be delivered so that enough cells must be transformed with an MCOLN1 gene therapy vector to overcome the anemic condition. The determination of the dose of an MCOLN1 gene therapy vector depends on the type of vector, how it is delivered, and the susceptibility and receptivity of the subject. All of these factors can be determined by routine dosing methods well known in the art.

In another embodiment, an agonist of MCOLN1 activity, e.g., a molecule that overcomes a mutation of an MCOLN1 gene that results in a defect in expression of functional MCOLN1, that is discovered using the screening techniques of the present invention, can be used.

EXAMPLE

The invention will be better understood by reference to the following Example, which is provided as exemplary of the invention and not limitation thereof.

Example

Identification of TRP Channel Family Gene Involved in Mucolipidosis Type IV

Analysis of candidate genes revealed that mutations in a novel member of the polycystin II family of the TRP channel gene family result in mucolipidosis type IV.

Materials and Methods

MLIV Families. Prior to initiating this study, approval from the institutional review boards at Massachusetts General Hospital, Harvard Medical School, the National Institute of Neurological Disorders arid Stroke, and Hadassah University Hospital was obtained. All patients or their legal guardians signed written informed consent to their participation in the study. We collected samples from 35 AJ and 5 NJ families. We cultured EBV transformed lymphoblasts and primary skin fibroblasts from patients and family members using standard conditions. We prepared genomic DNA and total RNA samples from cultured cells using commercial kits.

Physical Mapping. BACs were purchased from Research Genetics and cosmids were obtained from Lawrence Livermore National Laboratory (LLNL). STS content mapping, genotyping of MLIV families, and haplotype analysis was performed. Both the BACs and the cosmids were sequenced by a collaborative effort of LLNL, the Department of Energy Joint Genome Institute, and the Stanford Human Genome Center (SHGC). Placement of the markers D19S869, INSR, D19S592, D19S406, D19S901, D19S873, D19S76, D19S995, D19S912, D19S884, and D19S922 was performed by PCR of oligonucleotide primers using BAC and cosmic DNA as a template (FIG. 1).

Figure 1B:
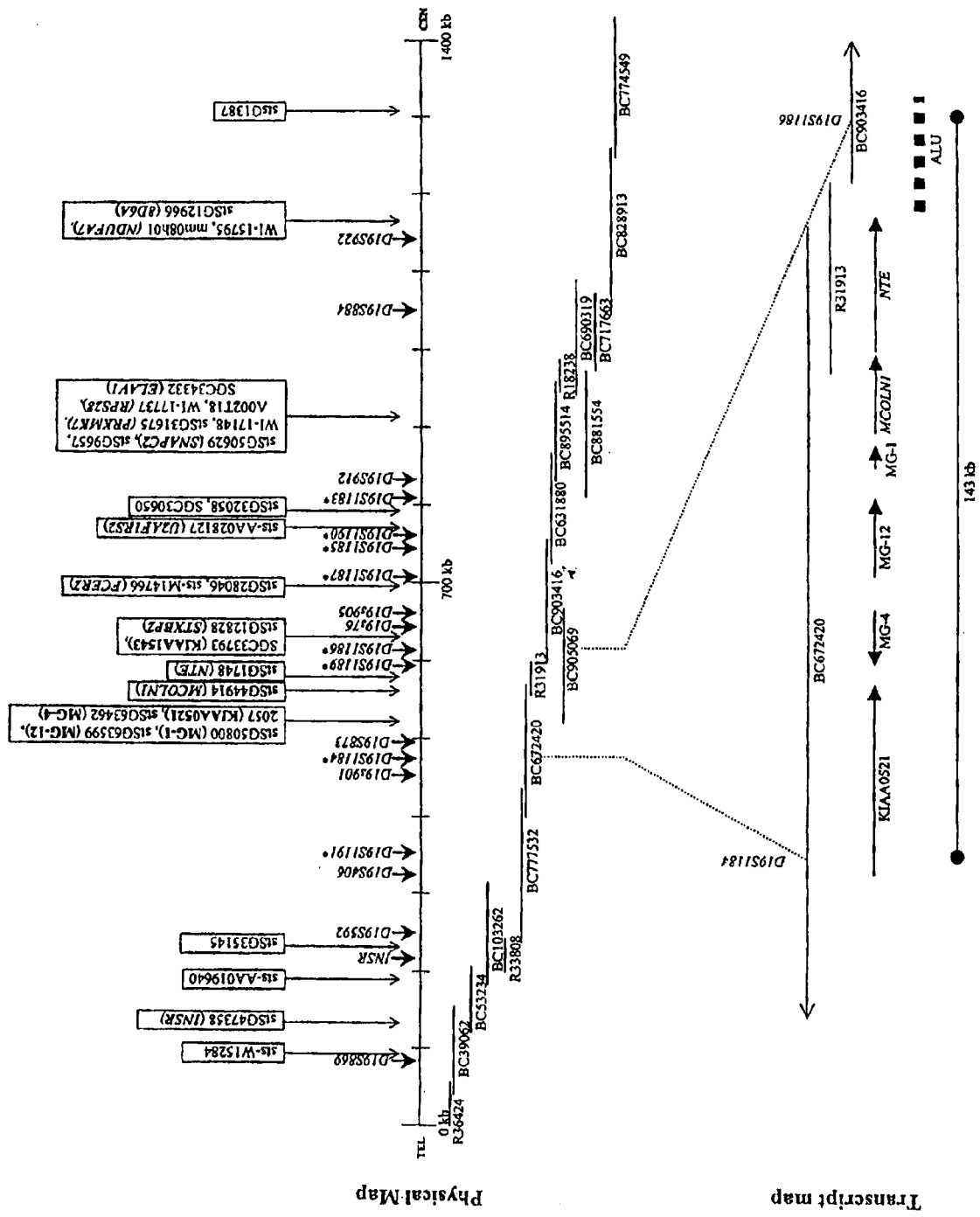

Expressed sequence tags (ESTs) were identified from GeneMap '99. To accommodate positional discrepancies, we chose to include ESTs that were within 4 cR of the original candidate region boundary markers of D19S406 and D19S912. This was accomplished by selecting a region on GeneMap '99 between the anchor markers D19S216 and D19S413 (FIG. 1B). Sequence of ESTs from unique UniGene clusters was obtained from GenBank, and oligonucleotide primers were obtained from the Radiation Hybrid Database. The ESTs were then localized on the physical map by PCR of the BACs and cosmids (FIG. 1B). The physical mapping of all ESTs was later confirmed from the individual BAC sequences as they became available.

As sequence from the region became available, we used the REPEAT program of the Wisconsin Package Version 10.0 (Genetics Computer Group (GCG)), with a window setting of 15, a stringency parameter of 13, and a range of 25, to identify di-, tri-, and tetra-nucleotide repeats. Once identified, the unique repeats were visually inspected to determine the likelihood that they would be polymorphic. Oligonucleotide primers were then designed manually to amplify the desired fragment of DNA. Twenty-seven simple sequence repeats (SSRs) were identified in the region of interest and were genotyped in a panel of 40 individuals to determine if they were polymorphic. These were localized in the BACs and cosmids initially by PCR, and the localization was later confirmed by sequence as it became available (FIG. 1B).

For the haplotype analysis, we studied 70 AJ and 10 NJ disease chromosomes, 79 non-MLIV chromosomes (obtained from AJ heterozygote carriers), and 26 control chromosomes (obtained from unaffected AJ individuals who married into MLIV families). All chromosomes were genotyped and haplotypes constructed with the following markers: D19S406, D19S1191, D19S901, D19S1184, D19S873, D19S1189, D19S1186, D19S76, D19S905, D19S1187, D19S1185, D19S1190, and D19S912. Haplotypes were constructed manually by visual inspection of markers across the region.

Exon Trapping. Restriction fragments from BC672420 were shotgun subdloned into the EcoRI site of exon-trapping vector pSPL3, and transfected into COS-7 cells. Spliced products obtained by RT-PCR were cloned into pAMP 10 using the UDG cloning kit provided in the Exon-trapping system (GIBCO BRL) and sequenced.

Full length MCOLN1 cDNA Sequence and Mutation Analysis. Total RNA from fibroblasts was used for RT-PCR with the following primers designed from the sequence of IMAGE clone 2517653 and GENSCAN-predicted exons: (SM-F3: 5' CGAGGGAGCGAGGTCGCAGTGACAGC 3' (SEQ ID NO: 6) from exon 1 and SM-R5: 5' AACACCCTC-CCCACCCAGTCTCCCC 3' (SEQ ID NO: 7) from exon 14). The PCR products were cloned into PCR2.1 or TOPO blunt PCR vector (Invitrogen) and sequenced. The mutation in genomic DNA on the major AJ haplotype patients was analyzed by PCR using primers mg2-EF4: (5' CAACCTC-TACTACCCTCTCCC 3'; SEQ ID NO: 8) and mg2-ER4: (5' AACAGTGAAGCCTCGTCC 3'; SEQ ID NO: 9). The 6434-bp deletion associated with the minor AJ haplotype was identified by using genome walking technology with the Universal Genomewalker kit (Clontech). The deletion boundaries were confirmed by sequencing purified PCR products generated using the forward primer mg2-GWF4: (5' CT GATATAAATG GCAGGCAGCTTTC 3'; SEQ ID NO: 10) at bp 226 of the genomic sequence (ACC: AF287270) and a reverse primer mg2-ER6: (5 CTCAC-CGTGCTGGAAGACAC 3'; SEQ ID NO: 11 in exon7 designed according to genome walking results. In order to identify mutations in the unique haplotypes, overlapping sets of PCR primers were designed and used for RT-PCR from lymphoblast or fibroblast RNA. We also designed primers to amplify each exon from genomic DNA. All mutations were confirmed by PCR of genomic DNA and sequencing in the patients and parents (when available).

Northern Analysis.Total RNA from fibroblasts or lymphoblasts was used for Northern blots. Fifteen micrograms of total RNA was separated by formaldehyde agarose gel electrophoresis, transferred onto a Hybond-N+nylon membrane (Amersham), and UV-cross-linked. The XhoI-EcoRI 2050-bp insert of IMAGE clone 2517653 was random primer labeled with $\alpha$-$^{32}$P-dCTP (GIBCO BRL) and used as a probe on the northern blot for MLIV patients and a human adult multiple-tissue northern blot (Clontech, MTN-I), as well as on a human fetal northern blot (Clontech, MTN Fetal II) to assess tissue distribution. We performed all hybridizations in hybridization solution (0.2M NaPO4, pH 7.2, 1 mM EDTA, 1% BSA, 7% SDS, 15% formamide) at 65° for overnight. The blots were washed twice in 40 mM NaPO4 (pH 7.2), 1% SDS, 1 mM EDTA for 30 min.

DNA Sequencing.Sequencing was performed using the AmpliCycle sequencing kit (Perkin Elmer) or on an ABI 377 automated DNA sequencer using BigDye terminator cycle sequencing kit. (DNA Sequencing Facility of the National Institutes of Neurological Disorders and Stroke).

Bioinformatics.We conducted database searches using BLAST (ncbi.nlm.nih.gov/blast on the World Wide Web). Sequences from Unigene (ncbi.nlm.nih.gov/UniGene on the World Wide Web) were used to confirm the MCOLN1 sequence. We performed motif searches using ProfileScan (isrec.isb-sib.ch/software/PFSCAN$_{13}$ form.html on the World Wide Web) and TMPred (ch.embnet.org/software/TMPRED_form.html on the World Wide Web) and alignment of protein sequences using Pileup (GCG) and Boxshade (ch.embnet.org/softward/BOX$_{13}$ form.html on the World Wide Web).

Accession Numbers.MCOLN1 cDNA, AF287269; MCOLN1 genomic sequence, AF287270; BC672420, AC008878; r31913, AC009003; BC903416, AC008763.

Results

Determination of the candidate interval. Following our initial report of linkage, we obtained a physical map consisting of overlapping BACs and cosmids from collaborators at Lawrence Livermore National Laboratory (LLNL). By localizing the linked markers on this map, we were able to narrow the candidate interval to approximately 550 kb. Our recent haplotype analysis utilizing 8 new genetic markers allowed further reduction of the candidate region to 143 kb between the markers D19S1184 and D19S186, a distance covered by two BACs (BC672420, BC903416) and one cosmid (R31913) (FIG. 1A). A 1.4-Mb physical map was constructed using 14 BACs and 4 cosmids (FIG. 1B). From this map, it was determined that the original candidate region that spanned DS19S406 to D19S912 covered approximately 520 kb and included BC777532 (GenBank Accession No. AC010324), BC672420 (GenBank Accession No. AC008878), R31913 (GenBank Accession No. AC009003), BC903416 (GenBank Accession No. AC008763), and BC631880 (GenBank Accession No. AC008812).

Of the 83 ESTs indicated on GeneMap '99 to lie between D19S216 and D19S413, 58 ESTs were found to represent unique UniGene clusters and were amplified using the 14 BACs and 4 cosmids as PCR templates. Twenty-eight of these were found to map within the 1.4-Mb physical map shown in FIG. 1B, of which 15 were found to represent known genes. The positive and negative PCR mapping results were later confirmed by sequence when it became available.

Isolation of Candidate Genes. A combination of exon trapping and EST mapping was used to identify MCOLN1 candidate genes. Once identified, we assembled the known ESTs and used direct sequence prediction of the genomic DNA in order to obtain the full-length cDNA sequences. In some cases, individual cDNA clones were purchased and sequenced to verify the predicted sequence. Examination of Genemap '99 showed 27 unique ESTs that potentially mapped to the 550 kb MCOLN1 candidate region. PCR of the BACs and cosmids demonstrated that six of these were located between the markers D19S1184 and D19S1186. Three of the six represented the previously identified genes KIAA052 1, neuropathy target esterase (NTE), and a small single exon zinc finger gene (AK001252), which we called MG-1. The remaining three ESTs represented novel genes and were named MG-2, MG-4, and MG-12. Exon trapping experiments yielded 11 unique exons from KIAA0521, NTE, MG-4, and MG-2. The exons that were trapped from MG-2 were found to match Unigene cluster Hs.12909 and we sequenced the IMAGE clone 2517653. We then designed PCR primers that flanked the putative start and stop codon and amplified a 2025-bp cDNA from control fibroblasts. Comparison of this sequence with the EST sequences enabled us to confirm that MG-2 contains a 1740-bp open reading frame (ORF) that encodes a 580 amino acid protein. The genomic structure of MG-2 was determined by aligning the cDNA sequence against the genomic sequence of BC672420. MG-2 is composed of 14 exons that span 13270-bp of genomic DNA. A schematic representation of the gene is presented in FIG. 1A. Systematic hybridization of northern blots containing patient and control RNA with probes made from MCOLN1 candidate genes showed a deficiency of the message for MG-2 in AJ MLIV patients homozygous for the major haplotype, heterozygous for the major and minor haplotypes, and homozygous for the minor haplotype (FIG. 2A lanes 2, 4, and 6, respectively), implicating this gene in the pathogenesis of the disease. This finding suggested that MG-2 was probably MCOLN1 and prompted us to search for mutations in the gene.

Identification of mutations in MCOLN1. In order to identify the mutations resulting in the decreased expression of MCOLN1 in the AJ patients, PCR was performed using cDNA made from patients that were homozygous for either the major or minor Jewish haplotype. PCR using primers designed to amplify the entire 2025-bp cDNA produced a single product of the expected size in control cDNA, several shorter bands in the major haplotype cDNA, and no band in the minor haplotype cDNA (data not shown). Sequence analysis of several clones obtained from RT-PCR of the major haplotype revealed the deletion of exon 4 and various partial deletions of exon 5. Analysis of genomic DNA using primers that flank exons 3 and 4 showed an A to G substitution at the 3' acceptor site of intron 3 (Table 1). This mutation is the likely cause of the apparent deletion of exon 4 in the mRNA. This substitution creates a KpnI restriction site that permits simple detection of the mutation by digestion following PCR using the primers mg2-EF4 and mg2-ER4 (FIG. 1). Following digestion with KpnI, carriers of the major mutation show the predicted 541-bp, 344-bp, and 197-bp fragments (lane 1), patients homozygous for the mutation show only the smaller fragments (lane 2), and controls show only the 541-bp fragment (lane 3) (FIG. 2B).

TABLE 1

MCOLN1 Mutations

| Haplotype | Nucleotide change | Mutation type | Amino acid change |
|---|---|---|---|
| AJ major | g.5534A>G | splice | — |
| AJ minor | g.511-6944del | 6434-bp genomic del | — |
| 18 (AJ) | g.511-6944del | 6434-bp genomic del | — |
|  | c.1334-1335insT | frameshift* | — |
| 20 (AJ) | g.5534A>G | splice | — |
|  | c.1346-1348delCTT | aa del | F408del |
| 44 (AJ) | g.5534A>G | splice | — |
|  | unknown |  |  |
| 48 (NJ) | g.9107A>G$^a$ | splice | 454-469del |
| 41 (NJ) | c.1461G>T | aa substitution | V446L |
| 42 (NJ) | c.429C>T | nonsense | R102X |
|  | c.1209G>T | aa substitution | D362T |
| 50 (NJ) | g.511-6944del | 6434-bp genomic del | — |
|  | c.598-599delCC | frameshift* | — |
| 53 (NJ) | c.639C>T | nonsense | R172X |
|  | g.9107A>G$^a$ | splice | — | g. mutations denoted using genomic sequence (AF287270),
c. mutation denoted using cDNA sequence (AF287269),
*translational frameshift mutations that result in termination codons,
$^a$bp substitution creates a new preferred splice acceptor site that results in the deletion of 15 AA.

Southern blots performed using DNA from a patient homozygous for the minor AJ haplotype showed the absence of a 3.4-kb BamHI fragment that spanned exons 2 through 5 (data not shown). PCR using several sets of primers outside this area showed that the DNA 1 kb upstream of MCOLN1 and downstream from exon 7 was intact. In order to identify the boundaries of the genomic deletion, we performed genomic walking with primers downstream of exon 7 and demonstrated that the mutation on the minor Jewish haplotype is a 6434-bp deletion (Table 1). The deletion extends from base pair 511 through 6945 of the MCOLN1 genomic sequence (AF287270) and spans exons 1–6 and the first 12-bp of exon 7. The extent of the deletion was confirmed by sequencing PCR products generated from the minor haplotype using the primers mg2-GWF4 and mg2-ER6, which flank the deletion (FIG. 1A and FIG. 2C). Patients who are homozygous for the minor AJ haplotype are missing the 541-bp fragment used for identification of the major haplotype and appear blank in FIG. 2B (lane 6). It follows, therefore, that patients who are heterozygous for the major and minor AJ haplotypes appear homozygous for the major haplotype (lane 4, FIG. 2B).

Figure 2D:
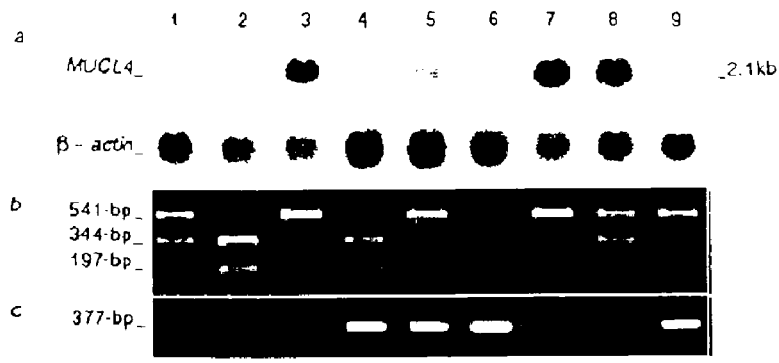
Figure 2D:
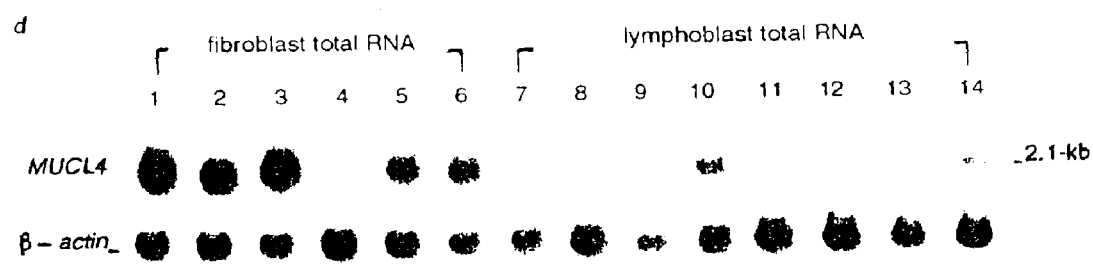

We also studied two AJ patients who are heterozygous for the major mutation and a unique haplotype (families 20 and 44) and one AJ patient who is heterozygous for the minor mutation and a unique haplotype (family 18). Given the results of our previous complementation studies implicating a single gene in both AJ and NJ patients, we also examined 5 NJ families (41, 42, 48, 50, 53) for expression of MCOLN1. Two of these families, 41 and 48, are consanguineous and are homozygous for all of the markers in the 19p13.2–13.3 region. Families 42 and 50 are heterozygous for unique haplotypes, and family 53 is heterozygous for a unique haplotype and the family 48 haplotype. Expression levels were evaluated in patient fibroblasts (FIG. 2A) in all cases except family 44, on whom only lymphoblasts were available (FIG. 2D). Expression of MCOLN1 was absent in the AJ patient from family 18 but normal in the patients from families 20 and 44 (FIG. 2A and 2D). In the NJ patients, high expression of MCOLN1 is evident in families 41, 42, 48, and 53, whereas there is no expression in the patient in family 50 (FIG. 2D). All 5 NJ patients were screened for the major and minor Jewish mutations, and interestingly the patient in family 50 was found to be heterozygous for the 6434-bp deletion (Table 1). Upon testing the parents, the mother was found to carry the AJ deletion mutation. The haplotype in family 50 for the 4 markers closest to MCOLN1 is completely different from the minor AJ haplotype and at this time we can not exclude the possibility that this deletion occurred twice on different genetic backgrounds. However, we feel it is more likely that the mother has AJ ancestry and that this haplotype is, in fact, distantly related to the minor AJ haplotype.

In order to identify MCOLN1 mutations in these patients, we designed overlapping sets of primers and amplified segments of the gene from patient lymphoblast or fibroblast cDNA. We also designed primers that would permit the amplification of each exon from genomic DNA. Mutations were identified for the unique haplotypes in families 18, 20, 41, 42, 48, 50 and 53 (Table 1). Two of the mutations cause frameshifts that predict truncated proteins (18 and 50). Mutations in 41 and 42 result in amino acid substitutions, both of which occur inside the putative transmembrane domains, and the unique mutation in family 20 results in the deletion of an amino acid that is located on the edge of the fourth predicted transmembrane domain. The base pair substitution in family 48 creates a new preferred splice acceptor site at bp 47 of exon 12 and results in the deletion of 15 amino acids between the fifth and sixth transmembrane domains. The mutations in families 42 and 53 carry base substitutions that create stop codons in exons 3 and 4, respectively.

Haplotype Analysis. Of the 26 SSRs identified, 8 were found to be polymorphic and were registered with the Genome Database as D19S1191, D19S1184, D19S1189, D19S1186, D19S1187, D19S1185, D19S1190, and D19S1183. Together with the markers from the previous study, we constructed a 14-marker haplotype that spans approximately 520 kb of the MCOLN1 region (Table 2). We observed five distinct haplotypes for the AJ population: a major founder haplotype that accounts for 72.9% (51/70), a minor founder haplotype that accounts for 22.9% (16/70), and three unique "odd" chromosomes that occur each once and account individually for 1.4% (1/70) of the AJ chromosomes. For each observation of the odd chromosomes in the AJ, it was noted that they occurred in conjunction with either the major haplotype (odd 2 and odd 3) or with the minor haplotype (odd 1).

We also constructed haplotypes for the five NJ families (families 41, 42, 48, 50, and 53. (Table 2). Although the families are not of AJ descent and are too small to provide evidence of linkage, the affected individuals in families 41 and 48 are homozygous across the 14 markers in our haplotype, which implicates a mutation in the same gene and suggests consanguinity. In addition, it is important to note that all of the affected individuals from the NJ families, with the exception of family 53, were utilized in complementation studies. These studies concluded that, although of differing ancestry, these patients carried a defect in the same gene as those AJ patients with MLIV. The two founder AJ chromosomes were analyzed to narrow the candidate region and pin-point the location of MCOLN1. An observed recombination event at D19S1184 coupled with four ancestral recombination events at D19S1186 allowed us to define a 143-kb candidate region between these markers (Table 3).

TABLE 3

EXTENDED HAPLOTYPE ANALYSIS

| D19S1406 | D19S1191 | D19S901 | D19S1184 | D19S873 | D19S1189 | D19S1186 | D19S76 | D19S905 | D19S1187 | D19S1185 | D19S1190 | D19S1183 | D19S912 | NUMBER |
|---|---|---|---|---|---|---|---|---|---|---|---|---|---|---|
| 207 | 4 | 152 | 8 | 120 | 6 | 4 | 3 | 216 | 2 | 3 | 6 | 3 | 175 | 28* |
| 207 | 4 | 152 | 8 | 120 | 6 | 4 | 3 | 216 | 2 | 3 | | | | 1 |
| 207 | 4 | 152 | 8 | 120 | 6 | | | | | | | | | 1 |
| 207 | 4 | 152 | 8 | 120 | 6 | 4 | 3 | 216 | 2 | | | | | 1 |
| 207 | 4 | 152 | 8 | 120 | 6 | 4 | 3 | 216 | 2 | | | | | 1 |
| 207 | 4 | 152 | 8 | 120 | 6 | 4 | 3 | | | | | | | 1 |

TABLE 2

Haplotypes and Mutations Associated with MLIV D19S Markers

| | 406 | 1191 | 901 | 1184 | 873 | 1189 | 1186 | 76 | 905 | 1187 | 1185 | 1190 | 1183 | 912 | Number[a] |
|---|---|---|---|---|---|---|---|---|---|---|---|---|---|---|---|
| AJ haplotypes | | | | | | | | | | | | | | | |
| Major | 207 | 4 | 152 | 8 | 120 | 6 | 4 | 3 | 216 | 2 | 3 | 6 | 3 | 175 | 51[b] |
| Minor | 211 | 4 | 161 | 3 | 126 | 8 | 10 | 4 | 234 | 1 | 3 | 1 | 5 | 179 | 16[b] |
| Odd 1 | 211 | 3 | 157 | 5 | 112 | 3 | 8 | 4 | 234 | 2 | 4 | 2 | 8 | 175 | 1 |
| Odd 2 | 211 | 4 | 159 | 3 | 114 | 5 | 7 | 4 | 218 | 2 | 3 | 2 | 3 | 175 | 1 |
| Odd 3 | 211 | 4 | 159 | 4 | 120 | 8 | 10 | 4 | 222 | 2 | 3 | 2 | 3 | 185 | 1 |
| NJ haplotypes | | | | | | | | | | | | | | | |
| NJ 41[c] | 207 | 3 | 152 | 8 | 112 | 7 | 5 | 3 | 216 | 2 | 3 | 3 | 3 | 177 | 2 |
| NJ 42 | 211 | 3 | 157 | 8 | 120 | 1 | 10 | 4 | 216 | 2 | 3 | 2 | 10 | 189 | 1 |
| NJ 42 | 211 | 4 | 156 | 8 | 120 | 8 | 2 | 3 | 218 | 2 | 3 | 2 | 10 | 187 | 1 |
| NJ 48[c] | 211 | 3 | 152 | 6 | 118 | 4 | 2 | 3 | 216 | 2 | 3 | 2 | 3 | 175 | 2 |
| NJ 50 | 211 | 3 | 161 | 5 | 112 | 5 | 12 | 4 | 216 | 2 | 3 | 1 | 8 | 175 | 1 |
| NJ 50 | 207 | 3 | 155 | 4 | 112 | 6 | 9 | 4 | 234 | 2 | 3 | 2 | 6 | 175 | 1 |
| NJ 53 | 207 | 4 | 152 | 8 | 120 | 7 | 4 | 3 | 216 | 2 | 3 | 2 | 6 | 175 | 1 |
| NJ 53 | 211 | 3 | 154 | 7 | 120 | 4 | 2 | 3 | 216 | 2 | 3 | 2 | 2 | 175 | 1 |

[a]Refers to number of chromosomes observed.
[b]See Table 3 for details
[c]Individuals from these respective families are homozygous across all markers.

TABLE 3-continued

EXTENDED HAPLOTYPE ANALYSIS

| | | | | | | | | | | | | | | |
|---|---|---|---|---|---|---|---|---|---|---|---|---|---|---|
| 207 | 4 | 152 | 8 | 120 | 6 | | | | | | | | | 1 |
| | | | | 120 | 6 | 4 | 3 | 216 | 2 | 3 | 6 | 3 | 175 | 1 |
| | 4 | 152 | 8 | 120 | 6 | 4 | 3 | 216 | 2 | 3 | 6 | 3 | 175 | 1 |
| 207 | 4 | 152 | 8 | 120 | 6 | | | | | | | | | 1 |
| 207 | 4 | 152 | 8 | 120 | 6 | | | | | | | | | 1 |
| 207 | 4 | 152 | 8 | 120 | 6 | 4 | 3 | 216 | 2 | 3 | 6 | | | 1 |
| 207 | 4 | 152 | 8 | 120 | 6 | 4 | 3 | 216 | 2 | 3 | | | | 1 |
| 207 | 4 | 152 | 8 | 120 | 6 | 4 | 3 | 216 | 2 | 3 | 6 | | | 1 |
| 207 | 4 | 152 | 8 | 120 | 6 | 5[b] | 3 | 216 | 2 | 3 | 6 | 3 | 175 | 6 |
| 207 | 4 | 152 | 8 | 120 | 7[a] | 5[b] | 3 | 216 | 2 | 3 | 6 | 3 | 175 | 1 |
| 207 | 4 | 152 | 8 | 120 | 6 | 5[b] | 3 | 216 | 2 | 3 | 6 | | | 1 |
| 207 | 4 | 152 | 8 | 120 | 6 | 5[b] | 3 | 216 | 2 | 3 | 6 | 3 | | 1 |
| 207 | 4 | 152 | 8 | 120 | 6 | 5[b] | 3 | 216 | 2 | 3 | 6 | | | 1 |
| 211 | 4 | 161 | 3 | 126 | 8 | 10 | 4 | 234 | 1 | 3 | 1 | 3 | 179 | 13* |
| 211 | 4 | 161 | 3 | 126 | 8 | 10 | 4 | 234 | 1 | 3 | 1 | 5 | | 2 |
| 211 | 4 | 161 | 3 | 126 | 8 | 10 | 4 | 234 | | | | | | 1 |

Analysis of 67 MLIV chromosomes representing the major and minor AJ haplotypes with 14 Markers. D19S406 is telomeric, and D19S912 is centromeric. Marker order was determined by genomic sequence data. The complete major and minor haplotype (marked with an asterisk) are shown in rows 1 and 20, respectively. Shading represents ancestral recombination events. [a]Represents an independent repeat expansion. [b]Represents an ancestral repeat expansion. Refers to the number of haplotypes observed.

Figure 3:
FIG. 3. Expression of MCOLN1 in human tissues. Multiple tissue blots (Clontech) of human tissues and human fetal tissues were sequentially hybridized with $^{32}P$-labeled cDNA probes for MCOLN1 and β-actin as indicated.
Figure 4A:
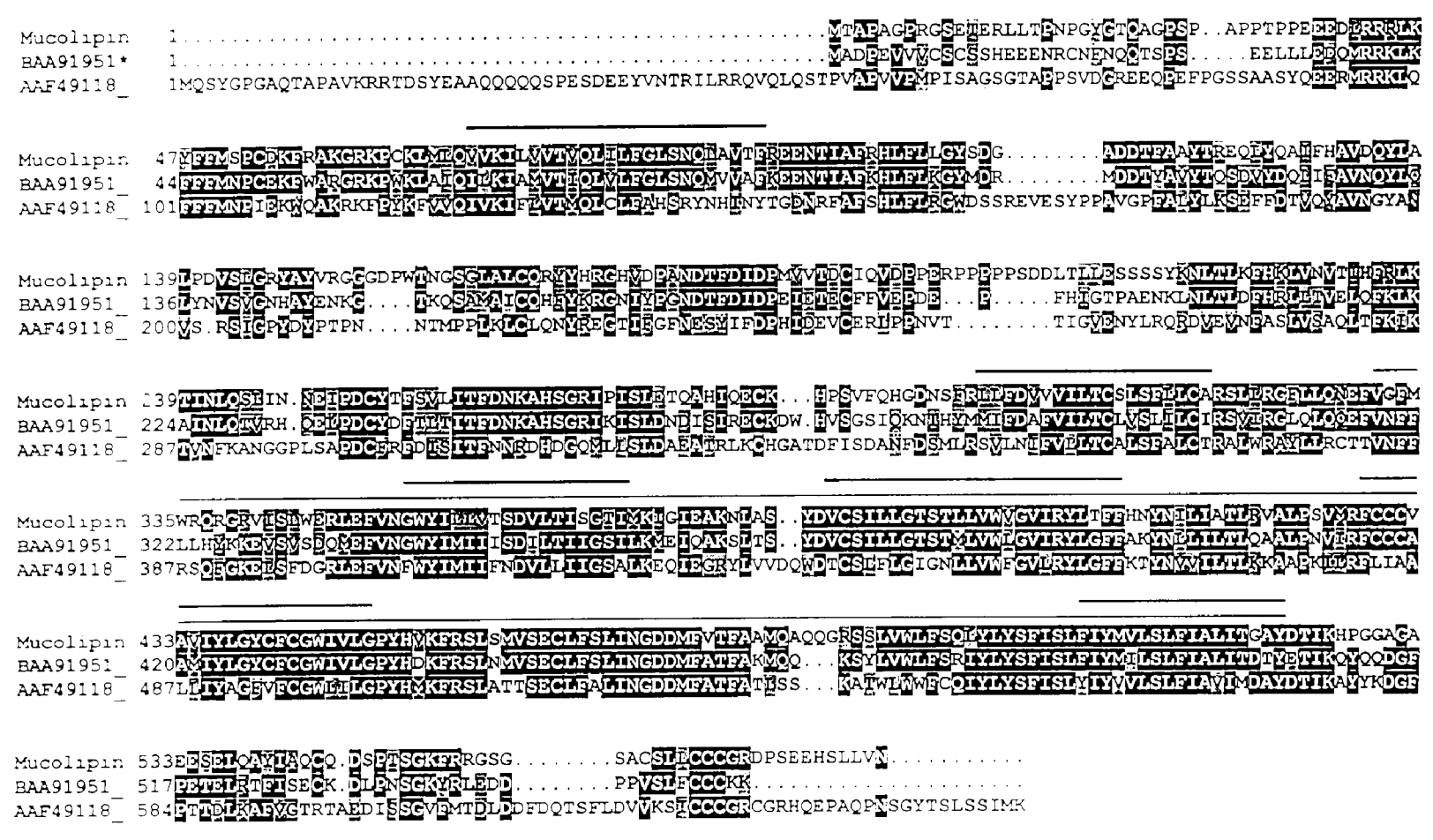

Characterization of MCOLN1. Northern analysis of various human tissues shows that the MCOLN1 message is ubiquitously expressed, with the highest expression levels in the heart, brain, skeletal muscle, spleen, kidney, liver, placenta and fetal tissues (FIG. 3). The predicted full-length protein, mucolipin, is 580 amino acids with a predicted molecular weight of 65 kDa. Structural analysis of the amino acid sequence predicts that the protein has 6 transmembrane domains, with both the N- and C-termini residing in the cytoplasm. Comparison of the amino acid sequence against known protein motifs and patterns at PROSITE identified a TRP (transient receptor potential) cation channel domain (aa 331–521) and an internal calcium and sodium channel pore region (aa 496–521). This TRP domain spans transmembrane segments 3–6, with the putative pore-forming loop between the fifth and sixth segments. Two proline rich regions were also identified (aa 28–36, aa 197–205) close to the N-terminus and between the first and second transmembrane segments, and a lipase serine active site domain at aa 104–114. A leucine zipper motif is located at the second transmembrane domain, and a nuclear localization motif at aa 43–60 (FIG. 4a). This protein also contains a putative di-leucine motif (LLXX) at the COOH-terminus which may serve as a late endosomal/lysosomal targeting motif.

Comparison of the amino acid sequence of mucolipin to GENBANK identified the likely Drosophila orthologue, CG8743, and a homologous human unnamed protein product, BAA91951 (FIG. 4A). Amino acid sequence identity between mucolipin and the Drosophila gene is striking with 38% identity (58% similarity) and nearly perfect conservation of the TRP channel domain and the channel pore region (58% identity). The gene encoding BAA91951, AK001868, is localized to chromosome 1 and the genomic structure was determined by comparison of the cDNA and genomic sequences. Comparison of the cDNA sequences of the two human genes showed that AK001868 does not contain exon 3 of MCOLN1. In order to determine if this was the result of a splicing difference, we used the amino acid sequence of exon 3 to search GENBANK using TBLASTN. The search was positive for the chromosome 1 genomic clone that contains AK001868 and predicts that exon 3 is probably alternatively spliced in this gene. Exon 3 was included in FIG. 4A and shows a similar level of homology with mucolipin and CG8743. Given the high degree of homology between MCOLN1 and BAA91951 (58% identical, 74% similar), we designated the chromosome 1 gene MCOLN1R1. Earlier work appears to mischaracterize MCOLN1. Bassi et al. (Am. J. Human Gen. 2000, 67:1110–20) describe a different sequence, which appears to be a mistake. NCBI has released sequence XP008934, which is a truncated (by 186 amino acids) computer generated sequence.

Figure 4B:
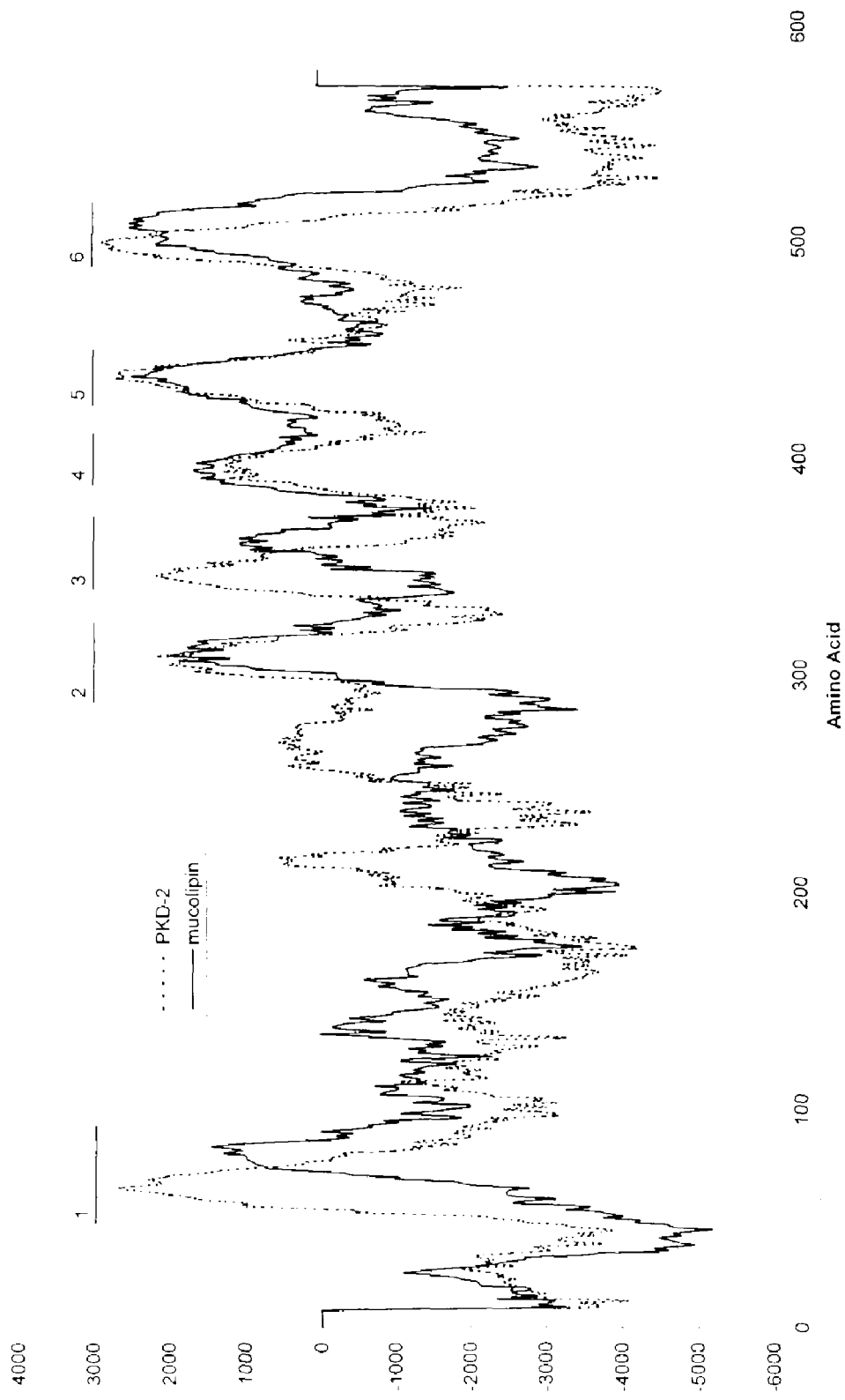

The Drosophila gene CG8743 was recently assigned to the polycystin II family within the TRP super-family (Littleton and Ganetzky, Neuron. 2000, 26:35–43). The TRP cation channel gene family includes proteins that contain 6 transmembrane domains and are presumed to be $Ca^{2+}$ transporters activated in a number of signal transduction related processes (harteneck et al., Trends Neurosci. 2000, 23:159–66). Proteins of this family are similar in structure to the family of voltage dependent calcium and sodium cation channels. A comparison of mucolipin to human PKD2 reveals only a limited similarity confined to the TRP channel domain, however, comparison of the hydrophobicity plot of mucolipin to the relevant section of PKD2 (aa 170–750) demonstrates an overlap of the transmembrane loop structures throughout the proteins (FIG. 4B). Unlike other cation channels, PKD2 and mucolipin have a large extracellular loop between the first and second transmembrane domain which probably indicates a similar unique function.

Discussion

MCOLN1 encodes a novel protein with 6 predicted transmembrane domains. A nearest neighbor dendrogram places the Drosophila homologue of mucolipin, CT25240, as an archaic member of the TRP channel superfamily in the Polycystin II family (Littleton and Ganetzky, supra). The predicted sequence of mucolipin is similar to PKD2 in the channel motif region (aa 361–540). There is also a high degree of similarity in the hydrophobicity plot between the two proteins. Mucolipin does not contain the long intracellular C- and N-terminal tails characteristic of presumed activation regions of other cation channels, but rather short tails that may indicate a different mode of activation. Based on the multiple prolines in the N-terminal region and following the first outer membrane loop and the lipase motif at AA 104, mucolipin may be activated by lipids involved in signal transduction processes.

Mucolipin may have a variety of functions in the cell which are reflected by the general biochemical and clinical aspects of MLIV pathology. The constitutive achlorhydria in MLIV patients and the selective vacuolation in stomach parietal cells of MLIV patients suggests that mucolipin is critical in HCl secretion (Sciffman et al., Prac. Natl. Acord. Sci USA 1998, 95:1207–12). Similarly, the observed vacuolation in corneal epithelial cells, acinar pancreatic cells, hepatocytes, chondrocytes, and renal duct cells (Berman et al., J. Pediat. 1974, 84:519–26; Folkerth et al., N. Neuropoth Exp Neurol. 1995, 54:154–64; Hammel and Alroy, J. Submicrose. Cynl. Pathol. 1995, 27:143–60) likely indicates dysfunction in ion channel activity and secretion. In the absence of mucolipin activity, inability to proceed with secretion may cause accumulation of solutes in intracellular vesicles and vacuolation. Storage bodies found in other cell types in MLIV, such as neurons and fibroblasts, (Folkertl et al, supra; Oddin et al., Pediat. Res. 1995, 37:67–92) may represent high degradation rates of the membranes that would normally contain the mucolipin channel and are destabilized due of its absence. Different phenotypes in different cell types in MLIV indicate that mucolipin may be similar to PKD2, which exhibits different subcellular localization and presumably different roles in the various tissues in which it is expressed (Foggensteiner et al., J. Am. Soc. Neptrol. 2000, 11:814–27). Moreover, the study of PKD2 in primary kidney cell cultures indicates that it is involved in lipid transport toward basolateral membranes (Charron et al. J. Cell Biol. 2000, 149:111–24). Similarly, mucolipin may be involved in lipid transport hence accounting for the abnormality in lipid transport reported in MLIV (Bargal and Rach, J. Inherit. Metab. Dis. 1997, 20:625–32; Chen and Pagano, Prac. Natl. Accord Sci. USA 1998, 95:6373–8).

A reduction in the activity of membrane-bound protein kinase C reported in MLIV (Tugeman and Boneh, Bochem. Mol. Med. 1996, 59:33–7) suggests that mucolipin participates in signal transduction processes. Mucolipin deficiency may lead to the sensitivity to chloroquine observed in cultured fibroblasts from MLIV patients (Goldin et al., Prac. Natl. Acad. Sci. USA 1999, 96:8562–6). This chloroquine sensitivity is possibly related to mucolipin's role in the restoration of pH balance to vesicles filled with this weak base. Mucolipin may play a major role in the development of white matter tracts and in the maintenance of neurons and retinal cell integrity as suggested by the pathology and neuro-imaging studies of MLIV patients (Frei et al., Neurology 1998, 51:565–9; Folkert et al, supra).

It is likely that examination of undiagnosed patients with MLIV-like symptoms, e.g., labeled "developmental delay of unknown etiology," will yield additional MCOLN1 mutations given the high number of mutations already found in a relatively small number of families. In addition, the observed variability in mutation type and location should permit the study of genotype-phenotype relationships in these patients. The fact that 2 mutations account for 96% of all AJ chromosomes makes MLIV amenable to population based screening. However, the development of specific tests for the remaining mutations is less effective due to their rarity. We have presented the complete 14-marker haplotypes of all known AJ and NJ MLIV chromosomes, which may provide an efficient method of screening patients suspected of having MLIV, particularly in the case of families with no known Jewish ancestry. This haplotype information will provide an invaluable and cost-effective tool for both diagnosis and directed mutation detection prior to sequencing the entire MCOLN1 gene, a costly and labor-intensive endeavor.

Finally, MLIV will be a useful model in which to study the role of a distinct ion channel gene in brain development and neuronal maintenance, corneal and retinal cellular function, and hydrochloric acid secretion.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values are approximate, and are provided for description.

All patents, patent applications, publications, and other materials cited herein are hereby incorporated herein by reference in their entireties.

What is claimed is:

1. An isolated nucleic acid molecule at least 20 nucleotides in length, wherein the nucleic acid shares at least 95% sequence identity with a corresponding sequence from SEQ ID NO:1 or SEQ ID NO:2.

2. The nucleic acid of claim 1, comprising a mutation relative to SEQ ID NO:1 or SEQ ID NO:2.

3. The nucleic acid of claim 2, wherein the mutation is selected from the group consisting of: (a) an A to G substitution at position 5534 of SEQ ID NO: 1; (b) a deletion from nucleotide 511 to nucleotide 6944 of SEQ ID NO: 1; (c) an insertion of T between nucleotide numbers 1334 and 1335 of SEQ ID NO: 2; (d) a deletion of CTT spanning nucleotides 1346–1348 of SEQ ID NO: 2; (e) an A to G substitution at position 9107 of SEQ ID NO: 1; (f) a G to T substitution at position 1461 of SEQ ID NO: 2; (g) a C to T substitution at position 429 of SEQ ID NO: 2; (h) a G to T substitution at position 1209 of SEQ ID NO: 2; (i) a CC deletion at 598–599 of SEQ ID NO: 2; and (j) a C to T substitution at position 639 of SEQ ID NO: 2.

4. The nucleic acid of claim 2, wherein the mutation is associated with development of mucolipidosis IV.

5. The nucleic acid of claim 2, wherein the mutation is an insertion in the nucleic acid.

6. The nucleic acid of claim 2, wherein the mutation is a deletion of the nucleic acid.

7. The nucleic acid of claim 2, wherein the mutation is a point-mutation.

8. The nucleic acid of claim 2, wherein the mutation is a nonsense mutation.

9. The nucleic acid of claim 2, wherein the mutation is a frameshift mutation.

10. The nucleic acid of claim 2, wherein the mutation is a missense mutation.

11. The nucleic acid of claim 2, wherein the mutation is an mRNA splicing mutation.

12. The nucleic acid of claim 1, which encodes a polypeptide having an amino acid sequence at least 95% identical to SEQ ID NO: 3.

13. The nucleic acid of claim 12, wherein the polypeptide has an amino acid sequence as depicted in SEQ ID NO:3.

14. The nucleic acid of claim 13 which has a nucleotide sequence as depicted in SEQ ID NO:1 or SEQ ID NO:2.

15. An expression vector comprising the nucleic acid of claim 12, operatively associated with a promoter.

16. The expression vector of claim 15, wherein the nucleic acid encodes the amino acid sequence as depicted in SEQ ID NO:3.

17. A vector comprising the nucleic acid of claim 1.

18. The nucleic acid of claim 1, wherein the nucleic acid is a single stranded oligonucleotide.

19. A method for detecting a mutation associated with a mucolipidosis, which method comprises
(a) contacting a sample suspected of comprising a nucleic acid having a sequence at least 95% identical to SEQ ID NO: 1 with an oligonucleotide of claim 18 under conditions that permit hybridization of the oligonucleotide to the nucleic acid, and
(b) determining the presence of a hybrid formed between the oligonucleotide and the nucleic acid; wherein said determining indicates the presence or absence of a mutation in the nucleic acid.

20. The method according to claim 19, wherein the mutation consists of an insertion in the nucleic acid.

21. The method according to claim 19, wherein the mutation is selected from the group consisting of: (a) an A to G substitution at position 5534 of SEQ ID NO: 1; (b) a deletion from nucleotide 511 to nucleotide 6944 of SEQ ID NO: 1; (c) an insertion of T between nucleotide numbers 1334 and 1335 of SEQ ID NO: 2; (d) a deletion of CTT spanning nucleotides 1346–1348 of SEQ ID NO: 2; (e) an A to G substitution at position 9107 of SEQ ID NO: 1; (f) a G to T substitution at position 1461 of SEQ ID NO: 2; (g) a C to T substitution at position 429 of SEQ ID NO: 2; (h) a G to T substitution at position 1209 of SEQ ID NO: 2; (i) a CC deletion at 598–599 of SEQ ID NO: 2; and (j) a C to T substitution at position 639 of SEQ ID NO: 2.

22. The method according to claim 19, wherein the mucolipidosis is mucolipidosis IV.

23. The method according to claim 19, wherein the mutation is a deletion of the nucleic acid.

24. The method according to claim 19, wherein the mutation is a point-mutation.

25. The method according to claim 19, wherein the mutation is a nonsense mutation.

26. The method according to claim 19, wherein the mutation is a frameshift mutation.

27. The method according to claim 19, wherein the mutation is a missense mutation.

28. The method according to claim 19, wherein the mutation is an mRNA splicing mutation.

29. A method for diagnosing a mucolipidosis, which method comprises
(a) contacting a sample suspected of comprising a nucleic acid having a sequence at least 95% identical to SEQ ID NO: 1 with an oligonucleotide of claim 18 under conditions that permit hybridization of the oligonucleotide to the nucleic acid, and
(b) determining the presence of a hybrid formed between the oligonucleotide and the nucleic acid; wherein said determining indicates the presence or absence of a mutation in the nucleic acid.

30. The method according to claim 29, wherein the mutation is selected from the group consisting of an insertion in the nucleic acid, a deletion of the nucleic acid, a truncation of the nucleic acid, a nonsense mutation, a frame shift mutation, a splice-site mutation, and a missense mutation.

31. The method according to claim 29, wherein the mutation is selected from the group consisting of: (a) an A to G substitution at position 5534 of SEQ ID NO: 1; (b) a deletion from nucleotide 511 to nucleotide 6944 of SEQ ID NO: 1; (c) an insertion of T between nucleotide numbers 1334 and 1335 of SEQ ID NO: 2; (d) a deletion of CTT spanning nucleotides 1346–1348 of SEQ ID NO: 2; (e) an A to G substitution at position 9107 of SEQ ID NO: 1; (f) a G to T substitution at position 1461 of SEQ ID NO: 2; (g) a C to T substitution at position 429 of SEQ ID NO: 2; (h) a G to T substitution at position 1209 of SEQ ID NO: 2; (i) a CC deletion at 598–599 of SEQ ID NO: 2; and (j) a C to T substitution at position 639 of SEQ ID NO: 2.

32. The method according to claim 29, wherein the mucolipidosis is MLIV.

33. A method for predicting the likelihood of developing MLIV, which method comprises
(a) contacting a sample suspected of comprising a nucleic acid having a sequence at least 95% identical to SEQ ID NO: 1 with an oligonucleotide of claim 18 under conditions that permit hybridization of the oligonucleotide to the nucleic acid;
(b) determining the presence of a hybrid formed between the oligonucleotide and the nucleic acid, wherein said determining indicates the presence or absence of a mutation in the nucleic acid; and
(c) establishing that there is a likelihood of developing MLIV if the mutation is present.

34. The method according to claim 33, wherein the mutation consists of an insertion in the gene.

35. The method according to claim 33, wherein the mutation is selected from the group consisting of: (a) an A to G substitution at position 5534 of SEQ ID NO: 1; (b) a deletion from nucleotide 511 to nucleotide 6944 of SEQ ID NO: 1; (c) an insertion of T between nucleotide numbers 1334 and 1335 of SEQ ID NO: 2; (d) a deletion of CTT spanning nucleotides 1346–1348 of SEQ ID NO: 2; (e) an A to G substitution at position 9107 of SEQ ID NO: 1; (f) a G to T substitution at position 1461 of SEQ ID NO: 2; (g) a C to T substitution at position 429 of SEQ ID NO: 2; (h) a G to T substitution at position 1209 of SEQ ID NO: 2; (i) a CC deletion at 598–599 of SEQ ID NO: 2; and (j) a C to T substitution at position 639 of SEQ ID NO: 2.

36. The method according to claim 33, wherein the mutation is a deletion of the nucleic acid.

37. The method according to claim 33, wherein the mutation is a point-mutation.

38. The method according to claim 33, wherein the mutation is a nonsense mutation.

39. The method according to claim 33, wherein the mutation is a frameshift mutation.

40. The method according to claim 33, wherein the mutation is a missense mutation.

41. The method according to claim 33, wherein the mutation is an mRNA splicing mutation.

42. A kit for detecting a mutation in a nucleic acid having at least 95% sequence identity to SEQ ID NO: 1, comprising an oligonucleotide of claim 18 that specifically hybridizes to or adjacent to the mutation, and a means for detecting binding of the oligonucleotide to the nucleic acid.

43. The kit according to claim 42, wherein the oligonucleotide is a labeled probe.

44. The kit according to claim 42, wherein the oligonucleotide hybridizes to a first site adjacent to the mutation, further comprising a second oligonucleotide that specifically hybridizes to a second site adjacent to the mutation, wherein the second site is on the opposite strand relative to the first site, and oriented relative to the first site such that both sites flank opposite sides of the site of the mutation, whereby the first and second oligonucleotides serve as primers for PCR amplification of the site of the mutation.

45. The kit according to claim 42, wherein the mutation is selected from the group consisting of an insertion in the nucleic acid, a deletion of the nucleic acid, a truncation of the nucleic acid, a nonsense mutation, a frameshift mutation, a splice-site mutation, and a missense mutation.

46. The kit according to claim 42, wherein the mutation is selected from the group consisting of: (a) an A to G substitution at position 5534 of SEQ ID NO: 1; (b) a deletion from nucleotide 511 to nucleotide 6944 of SEQ ID NO: 1; (c) an insertion of T between nucleotide numbers 1334 and 1335 of SEQ ID NO: 2; (d) a deletion of CTT spanning nucleotides 1346–1348 of SEQ ID NO: 2; (e) an A to G substitution at position 9107 of SEQ ID NO: 1; (f) a G to T substitution at position 1461 of SEQ ID NO: 2; (g) a C to T substitution at position 429 of SEQ ID NO: 2; (h) a G to T substitution at position 1209 of SEQ ID NO: 2; (i) a CC deletion at 598–599 of SEQ ID NO: 2; and (j) a C to T substitution at position 639 of SEQ ID NO: 2.

* * * * *

SEQUENCE LISTING

```
<160> NUMBER OF SEQ ID NOS: 11

<210> SEQ ID NO 1
<211> LENGTH: 13270
<212> TYPE: DNA
<213> ORGANISM: Homo sapiens

<400> SEQUENCE: 1
tctcacttac cccttgctct tcaaagccca tacagtaggt atacaagtgg acaaaaaaag        60
ttgctcattt atgcaatcaa caaacatctc tggattgctg gggtctcagc agggaacaag       120
ataaatatgg cctcgacctg catggagctc atagatacta aattcagaat acttaaaaaa       180
taattacggg gtatagtaca ttctaggaga agcataacaa gacttctgat ataaatggca       240
ggcagctttc tcaatgaagg attttgtaat cccaataatc actaatttaa taatcagtac       300
tgtttgccca gccttatgcg atagtttttg cattctctca tttaatcctc tcaacagccc       360
cagtaggtag atgactttga atatccccat tttgcaaatg agaaaattga ggcacatttt       420
tttttttttt tttagacagt cttgctctgt tgcccaggct ggagtgcagt ggtgtgatca       480
```

```
tagctcactg cagcctcgac ctcctgggct caagcgatcc tcccaccttta gcctcccgag    540 tagctgggat tgccggtgca tgccaccgcc cactgcgctc agcttggagt tgaagggact    600
ctggaagatg tagaagtggc attgtcagtg cctagattta aatcccaatt gccctccagg    660
gtccaaattc ttaaccatta cgctccaggg caaaagtatg caaaggctct ggggctatag    720
aaagatgagc tttggatgga ggtaggagcc agatcagagg gccctgatag acgagagtgg    780
ggactctgcc tgtcattaca gagcaatggg aagccgaggc caggttctcg caggaaggat    840
aggaattatt ctttgaagat gcttgtggct gctgggtaga gagtggagtg gagggaggct    900
gagatcgggg aggaggttgc tgcaaagatc caggccagga atgttggaag actctgggct    960
gggggccatg gggtggggat aagtggttct atttgataca taattaggaa atcgtgtttg   1020
ctgaagatgc gcaggagaag ggtaaaagga gtttctggga gaaagaggaa gacagcgttg   1080
agatagtagg cagggtcatc accaggcacc aaggaggata aggggtcaag ctctggacat   1140
ggaagtcaca agcctggcac cggattcggg gcatggccgg gagccagggc agagctcgtc   1200
gttgccaaac tcagagtcag cccatccccc gccacccaga gcgcgtcggc gctaggacct   1260
agcgactgcc ttcgacccag agggcgccgg cagaggcacg catgcgcgct gttccggcag   1320
gggttgtcgt ggcgcagggg gcgggaccag aggcggtcac gtgagggggct ctgggctacc   1380 gggtcacgtg accgaggcac agatcagctg atgccggagg gtttgaagcc gcgccgcgag   1440
ggagcgaggt cgcagtgaca gcggcgggcg atcggaccca ggctgccccg ccgtacccgc   1500
ctgcgtcccg cgctcccgcc ccagcatgac agccccggcg gtccgcgcg gctcaggtga   1560 gggcgcgggc ggcaccgtgg ggccccgaac tcaggcgggc gggctgtgtc tcccacctgg   1620
ggcggcggag ctcctagtct cttttttttct aagctccagc gctgactttt cacggtggag   1680
aaaagggcag acggctccta gaacttgggc ggcgggtggg caccagcctc tccaattctt   1740
cctcctgaac ccaggctctg ctgggttccc aaactcaggc agggatcgcg ccgggccgcc   1800
agcttctccc tctggggcgg cgaggttcct gggattccca ctgggagcct aggttccgat   1860
tgctcaactt cgtctggaac tcagacagcg ggcaccagct tctccaaccc gcacgtgaga   1920
ctcccaggct tcccctcctg attccagggg acaaatgctc agcttcccta agctcaagcc   1980
tggagagctg gagggattgc ccccaggcga ttaactcagt tttagctttc caaaccgctg   2040
gaagcgcagc cttcttaaat tcgggcttct agccaattct gatgccaccc ctcctcgggg   2100
aggctggagg aagacccctt gtgttagctt ccccttctgg agctagctgg ggaccccctac   2160 ctgatagatg tcccggtgtc ccagctagta gggtctgggg tgggttagct gtaatctcag   2220
ctctgtaagc gggccctgcc ctctggcttt gtcgtaaaca gccacagcag catctcattg   2280
caaagggagg ggccgggaac ttgtccctct ctgcaaggga ggttctgaca gtgcacacat   2340
ttatcctgac tgcttttgcta ggcaggaggc caggccctag aaagcagcac ggggccaggc   2400
cctagaaagc acatccccat ggggtgtgna cagggacagt tttgggctac tgtgactggt   2460
tttgactcca gcagttgctg aaagcttaga tctaaccatt aggctggaaa aaataaaca    2520 gtgattagaa cagcttgtgt ttgctgaaga ggtctttatc tgctgtgtct cactgaattc   2580
tcagagcagc ttcaggatct caacctcaag gctcaggag agggtggact tttttttttt   2640
ttaataaact ttttttttgtt gcccaggctg tagtgcagtg cataatcct agctcattgt   2700 aacatcgaac tcctgggctc aagtgatcct cccaactcag cctcccgggt agatgggtc    2760 ccagctacta actacgggca tgagccgtca cacctgacta tttaaaaaa atgttttttt   2820 tttgtagaca gggaggtctc gctgtattac ctaggctgga tcctcccacc ttggcctccc   2880
```

```
aaagccgttg ggataacagg catgagccac tgagcccagc caagggg tcg ccttttaaa    2940
atttccactc ttcagatgag gagatggagg ctcagggagg tacctggagt caacctactg    3000
taaagtggca ggtctgggat tgatgctag ggctgcatga tttctaggag ctggtgcttt    3060
tcagggagat aaaatgagtc tttagcgaat gtgttccatt attattactt atgttgtcaa    3120
ttacctcttc tccaggtcct tggcttctga gagtgtcagc tgatgggcca ggttataatg    3180
aacccagagg tcatcttttg ggtatttgtc cagacaaacc tagaatacag gctgagttct    3240
atgctcatgt ctggaagctg gagttgggat aagcccagca ggcttgaacg cccagtgaaa    3300
agccagtggg agcagttcat tctctcccca ctgatcaata cgggaacat tgatgaaatg    3360
ttctgacatt caccatggac cagcccctgt gatcaatgct tcataagcat ccagtcctta    3420
gcgttcccat gagacatatt attgccccat ttcgcagatg aggaaactga ggctcagaga    3480
gctggtgagc aggaggggca ggaatcagcc caggccctgt acctcccaaa cccaaactca    3540
taacctctga gcaggacggg tgcatagata cctacaatgt cacaggtttt ctggtttttct    3600
ttagacctct cagagctctt ccttggcagg agcatgggga catgaagata gggcgtgtgc    3660
tgccttcctg gttggagaaa ggggaaaagg ggagttgccc aggcctcacc ccagtgccct    3720
ctcctattcc cacagagacc gagcggcttc tgacccccaa ccccgggtat gggacccagg    3780
cggggccttc accggcccct ccgacacccc cagaagagga agaccttcgc cgtcgtctca    3840
aatacttttt catgagtccc tgcgacaagt ttcgagccaa gggccgcaag ccctgcaagc    3900
tgatgctgca agtggtcaag atcctggtgg tcacggtgca ggtgaggcca gccaagcagg    3960
ggccccagct gaaggccacc tgtggctgct gtgctccttg aagagagtct taaagcagca    4020
ctttggaagg ccgaggccgg tggatcgctt gaggctggga gttcaagacc agtctggcca    4080
gcatggtgaa acccccatctc tactaaaaat acaaaaaaat tagccgtgcg tggtggcggg    4140
tgcctgtaat cccagctact tggcaggctg aggcaggaga atcgcttgaa ttgggaggcg    4200
gaggttgccg tgagctgaaa tcatgccact gcactccagc ctgggcaaca gagcaagact    4260
gtctcaaaaa aaaaaagaag ccgactctga ggctcagaga ggttaggaga cttgcccaaa    4320
gtcacacagc aatagaacat tgggagctgg gatttgaacc caggcagtct gacaccatgt    4380
tgacccaatg gctgcacaga tagttctccc tcccccatgc cagaccctgt gctgggctct    4440
gggaacccca agatgaatca gacccagcca ctgccctaag tgcttacttc atgttttggg    4500
ctgactttag catgtcacca tgcctctaat tttccctctg aaaagggacc caattgtcca    4560
ggcatggtgg ctcatgcctg taatgccagc actttgggag gctgagttgg gtggatcatt    4620
tgaggccagg agtttgagac cagcctggcc aacattgcaa acccccgtct ctactaaaaa    4680
tacaaaaatt agctgggttt ggtggcaggt acctgtaact cagctactca ggaggctgag    4740
acaggagaat tgcttgaacc cagggggtgg aggttgtagt gagctgagat cataccatgg    4800
cactccaact tgggcaacag agtgagactc tgtctcaaaa aagaaaagaa aagggaccca    4860
gtcatggtac ttaccctgaa agtttgggtt aacacagaa tcggacatcc agtaaacatt    4920
taatgaacgt tagtccctgc agtgagatag atgagtcccc accctgtgtt gtacgggga    4980
ggacacagtg gtgggcgtgg catggagctt atgccaggag gtggggtgaa attaatcaaa    5040
gcaaagaaat gcacaagtga aatccgtgtt tgtggcccaa gttagcaggg ccctgcccca    5100
ccccagtgga catctgcagg gccctccctg tcctcttcca gggcctgtgc cctgagggag    5160
atacaccca accccatcc tagccatgcc aacctctact accctctccc cagctcatcc    5220
```

-continued

```
tgtttgggct cagtaatcag ctggctgtga cattccggga agagaacacc atcgccttcc    5280
gacacctctt cctgctgggc tactcggacg gagcggatga caccttcgca gcctacacgc    5340
gggagcagct gtaccaggcc atcttccatg ctgtggacca ggtgctggtg ggcgggcagg    5400
tgctggtggg caggcaggtg caggtgggcg gcaggtgca gttgggcggg caggtgctgg    5460
tgggcgggca ggtgcaggtg ggtgggctgc agagagcggg ccggactcac aggccctccc    5520
cttctctgcc cacagtacct ggcgttgcct gacgtgtcac tgggccggta tgcgtatgtc    5580
cgtggtgggg gtgacccttg gaccaatggc tcagggcttg ctctctgcca gcggtactac    5640
caccgaggcc acgtggaccc ggccaacgac acatttgaca ttgatccgat ggtggttact    5700
ggtgagtggg caggacgagg cttcactgtt gggagcctga gctgctggga ttaaaatcaa    5760
cagctgtggc tgggcacggt ggctcacgcc tataatacca gcactttggg aggctgagga    5820
ggaaggattg cttgaggcca aagtttgag accagcctgg ccacgtagg aagaccttgt    5880 ctctacgcac aaacaaatta gctgggcgtg gtggcgtgcc cctgtggtcc cagctactca    5940
ggaggctgag gcaggaggat cgcttgagtc cgggaggttg aggctgcagt aagctatgac    6000
cacgctgctg cactccaccc tgggtgacag agtgagaccc tgtctcaaaa aaaaaaaaaa    6060 aaaaaaaaa caagtatgct tagtgtgagt gtgactcttg ccacgtagaa agcaccagat    6120
gttatatttt aatatggctc attcagtaaa acatccgcag gcccagagag tgccaggcct    6180
gtaggaatga cccaaccctg gggaagcaca gggaagaagg ccactgggga ctctggggag    6240
accagcctgg cctccccggc cccctgaggc ccttccctga ctccctgtcc ttagactgca    6300
tccaggtgga tcccccgag cggccccctc cgcccccag cgacgatctc accctcttgg    6360
aaagcagctc cagttacaag aacctcacgc tcaaattcca caagtactgc ctgctcactc    6420
gaggggggcc caggtggggg gaggcagcac actaggcact ctcaccccag caactacttc    6480
cctaaggtgg ggacagggcc ccccgcccg cgctggtgcc tgctgggtga gcacttcccc    6540
tgccagctgc agagtcagca cgtggcaggg gacgctggca cttggggccg aagggaccc    6600 gaagacgccc ctgaccctca cccgagcctc ctgcctaggc tggtcaatgt caccatccac    6660
ttccggctga agaccattaa cctccagagc ctcatcaata atgagatccc ggactgctat    6720
accttcagcg tcctggtgag gccccccggg aacccacagg gctcctgagt tccagggcag    6780
ggacctggtc agggagtgtc ttgggagcac tggccaaggg caagcgtgcg ggtgatgagg    6840
gagggagccc gggtctgtc aggccacctg tcatgtggac cttggggctt ggggctgcca    6900
aggtttactc tgcccccaac tggcccccac agatcacgtt tgacaacaaa gcacacagtg    6960
ggcggatccc catcagcctg gagacccagg cccacatcca ggagtgtaag caccccagtg    7020
tcttccagca cggtgagccc ctgagcccca gaccagcact gaccagggc cctggcctgt    7080 cctgggattc cccaagcccc agatcagcgc tgcctggggg ccgtgacctc cccaggaatc    7140
cgctgagcct cagatcagca cagaccaggg acccgtcct gtgctgagat cccccaagcc    7200
ccagaccagc actgaccggg gttcttgact caccccaagc aagccctgag cccactgacc    7260
aaccaaaacc agccgtgcag cccctaggt ctccagcctg gctggcacc aatgctagcc    7320 tcccaaggct ccatgccatc cttggcccta cccgctctgc cctccccgca ggagacaaca    7380
gcttccggct cctgttgac gtggtggtca tcctcacctg ctccctgtcc ttcctcctct    7440
gcgcccgctc actccttcga ggcttcctgc tgcagaacgt gaggcttctg cgtcatgtgt    7500
gctggtgtcc tccccgcctg gccctgggc gataaaagcc agggctttga gggtcctgtg    7560
cctggtcagg ccctcacccc gcctgccttc tgcaggagtt tgtggggttc atgtggcggc    7620
```

```
agcggggacg ggtcatcagc ctgtgggagc ggctggaatt tgtcaatggc tggtacatcc   7680
tgctcgtcac cagcgatgtg ctcaccatct cgggcaccat catgaagatc ggcatcgagg   7740
ccaaggtgcg tcctgccaac accctgggcc ccaggtccca tccctgctgt cagtgcctat   7800
ccggggccat atcctccccc aggccccccca aaggaagggc tgggccagat aggttgacgc   7860
agctcccacc cgcagaactt ggcgagctac gacgtctgca gcatcctcct gggcacctcg   7920
acgctgctgg tgtgggtggg cgtgatccgc tacctgacct tcttccacaa ctacaatgtg   7980
agttttgcac atgcagctgg gccttccaca tggttactcc acaccctcca aataaatccc   8040
tacacacgca gccctcacca gccccggcca atggccccctt gcaagcctcc tcctcctacc   8100
tgcccacacc agatatatct gtcactgcac ctgcgcgggg ccccgggagc ctgctccttt   8160
gtgcccaccc agctgagtct agccgtgcgt tgccctcgga ccccctcaga cgtggccacg   8220 cccctctag gcacccactg gctcccatga ccacaccggc tgtgccctcg gcaaggcccc   8280
gcccctccca acccatctg ggtgcccaca gctgacctga gttgtggcca caccctcaac   8340
gaggctccct ctgccccaac ccagatcctc atcgccacac tgcgggtggc cctgcccagc   8400
gtcatgcgct tctgctgctg cgtggctgtc atctacctgg gctactgctt ctgtggctgg   8460
atcgtgctgg ggccctatca tgtgaaggta catctaaccc ctgatgtccc tgacattgac   8520
cctgtgacct tgtcattgac actgtgaccc ccagatgacc ccttggtgac tgctgggagt   8580
ctgtccactg tcccctgtgg tccttggtga ccctgacact gaccctgtgc cattattgtt   8640
gtcacagttg ttgatgaccc tatttcgacc tgaattactc ccctcctgct ctatctaccc   8700
agaccctagg tcggccctgt ggccctgtca ttgacccgtg gtcccggcca ttcacatggg   8760
accccagcct gggacctggc cattcacata gtgaccccag cctgggaccc ggccattcac   8820
gtgggacccc agcctgggtc ccggccattc acgtgggacc ccagcctggg acccggccat   8880 tcacagggc cctagcctgg aacccgacca ttcacatggt gaccgcagcc cgggacccgg   8940
ccattcatgt ggggccccag ccaccagctc ctagccattt gcatgggacc ccagcctgac   9000
cccagccccc ggttcctggc catgccttgg ctccctctga cccgccgcc cctctggcag   9060 ttccgctcac tctccatggt gtctgagtgc ctgttctcgc tcatcaatgg ggacgacatg   9120
tttgtgacgt tcgccgccat gcaggcgcag cagggccgca gcagcctggt gtggctcttc   9180
tcccagctct acctttactc cttcatcagc ctcttcatct acatggtgct cagcctcttc   9240
atcgcgctca tcaccggcgc ctacgacacc atcaaggtca gccgcatgca cccagccctg   9300
agctcgggct ctgggtgccc tggagtctgc catgagggg tcttggggac accgcagggt   9360
gaacagagaa gacccaggag agaatatggg agactctatg aaaccaaaaa gagggtggtt   9420
cagaactggg gggcgcaggg ggatgtcaag gtgggcttgg gccaggaggg ggcctgagtc   9480
agtctttgcc aacagggcaa ccgagtcata gagtttattt atttatttgt ttatttgaga   9540
cggagtcttg ctctgtcacc caggtggag tgcagtggtg cgatcttgac tcactgcaac   9600
ctccacctcc cgggttcaag caattctgtc tcagcctcct gagtagctgg gactacaggc   9660
acacgccacc acgtccagct aattttttgta tttttagtag agatggcatt tcaccgcatt   9720
ggtcaggctg gtctcaaact cctgcctcag ggagatctac tgccttggcc tcccaaagtg   9780
ttgggattac aggcgtgagc caccacgccc ggcctatttt attttattat taaagtattg   9840
ttctttattt tattagagac aagggtctca ctgtgttacc caggctggtt tcaaactcct   9900
gaggtcaagt gatcctccca ctttggcctc ccaaagtgct gggattacag gcgtaagcca   9960
```

```
ccacacccag cctattatta ttatttttttt tttgaaatgg aatcttaccc tgtggcccag   10020
gctggagtgc aatggcatga tctcggctca ctgcaacctc caccttctga gttgaagcga   10080
tccttgtgcc tcagcctcct gagtagctgg gattacttgc acgtgccacc acacctggct   10140 aattttttgta ttttttactag agatgggggtt tcaccacgtt ggccaggctg gtctcgaact   10200
cctgacctca ggtgatccac ctgccttggc ctcccaaggt gctgggattt caggcatgag   10260
ccactgaacc cagctaagtc atacagtttc aatgaccttg tcattgaccc tgggacgttg   10320
ccattaacat ggtgatcctc agctggcccc attcctatgg cggacctcta aaaacccaac   10380
cctgacccca gcccccagcc atgccccga ctccctctga ccctgcccaa ggttagcttc   10440
tttatttatt tattttttttt gagacggagt ctcgctgtgt cacccaggct ggagtgcagt   10500
ggtgcaatct cggctcactg caacctctgc ctcccgggtt caagcgattc tcctgcctca   10560
gcctcctgag tagctgggat tataggcaca cgccaccatg cctggctaat ttttgtatttt   10620 ttagtagaga tgggggtttca ccatgttgac caggctggtc tcaaactcct gaccttgtga   10680
tccgcccacc tcaggctccc aaagtgctgg gattacgggc gtgagccact gtgcccggcc   10740
caggttagct tctgagcagt aaaactgggc tcaacccagg gctgtctgat tccagaagcc   10800
gtgctcctaa cccctctgtc ctcagtttag tagggtggct gggaacagtg gtttccctgc   10860
aagctgcaag ggtcagggga cagagcagga tgcggaagtg gcaggtagat aggattcttt   10920
cagcagatat atctaagggc caagatctgt gctgggttct gggcatggag gaaaatcagg   10980
tgtgcatgat ccgtccaagg cctgtgggca aggatggcac aggaacagac atcccatgac   11040
caatgaccta cttgtaacag gtatgaagga agagtggaag gttgcagagg gaccccctgct   11100 ttagattggt atgacaggag atccaggaga gcttctagaa tgttctatcc atcactagtc   11160
tctagcccta tgcagctatt taaattttga ttttaattcc ggctgggcac ggtgactcac   11220
gcctgtaatc ccagcccttt gggaggccga ggggggggtgg gggtggatca cctgaggtta   11280
ggagttcgag accagcctgg ccaacatggc aaaacccat ctctactaaa aatacaaaaa   11340
attagcggac gtggtggcag gcacctgtaa tcccagctac tccggaggct gaggcagtag   11400
aattgcttga acctgggacg tagaggttgc agtgagccga gatcaagcca ctgcactcca   11460
acgtgggcga gagaccgaga ctctgcttca aagacaaaac aacaatttttt taaaaatttt   11520 aattcaaatg aagtacaatt gcaaatttag cctctgactt gcaccatcct gtatccagtg   11580
ctcaaaagcc agtgtggctg gtggctgcca tattggacag catagatatt gaatacttcc   11640
atcgcctcta gactgaagag atgggagccc aggggcagtg caccgagggg aaggaatagc   11700
taaagcaaag gtctagtagc ctgaaaaaac ttggagaaaa gatggcccct ccatgaggcc   11760
gagtgagagg aaggaagcct tggctgggac cctgccacat ccaatgtcac cggcagatgg   11820
gtacaccccc ttttcccccat gcatggattc agctgtccca cagacacatt gactcaggcc   11880
cttgaaacta cttcctgtct tgccttagca cgtagacatc acacacatgc atccactcag   11940
gtgggcagtc tcaggccctg ctcccactgc tgtgctcagc gtgcatccag ctcactcaat   12000
agatggtttc tgagcatcga ggtcatgtca gccctggctc taggtctgta ggtgctggac   12060
ctacagcaga aggcaaagac acagactggc aaagacacag cttgtatcca ggttcagggg   12120
tcagggaagg tccctctgtg caagcaaact gtggaacaac gggtgagca ggcccagcaa   12180 gtgcaaaggc ccggaggtgg gaagcgatgc agatatggct ggaggggagg gcggacttca   12240
agggccttgg aggttgggag ccactttcag gctgagcctc ccggcttctc tccccagcat   12300
cccggcggcg caggcgcaga ggagagcgag ctgcaggcct acatcgcaca gtgccaggac   12360
```

```
agccccacct ccggcaagtt ccgccgcggg agcggctcgg cctgcagcct tctctgctgc    12420
tgcggaaggt tcgagtcccg ggtctggcac attcagattg gaggttacgg aatggggaaa    12480
ggggagcgag ccagagaaaa ctgacgcccc tcttccctgc ttccttcctc cagggacccc    12540
tcggaggagc attcgctgct ggtgaattga ttcgacctga ctgccgttgg accgtaggcc    12600
ctggactgca gagaccccg  cccccgaccc cgcttattta tttgtagggt ttgcttttaa    12660
ggatcggctc cctgtcgcgc ccgaggaggg cctggacctt tcgtgtcgga cccttggggg    12720
cggggagact gggtggggag ggtgttgaat aaaagggaaa ataaatgtgt cgttttcatt    12780
tttagcggga ggagcagtcc ttgcgttaag cggtgtgagg cccttaagg  cgcggccaca    12840 ctcagcatgg cggcctcagt cggccttcca agcatggcgc ggggaggagg ggtgggaggg    12900
tcgggaggga ctgcggtgcg actaggagtg aataatttaa aggggccgcg cctgcggagc    12960
cgggcggaac gctagcggtg ttggcgcgga gtggaccccg gctgcggccc ctgggtgagt    13020 ctgggttttcc gttagcctcg caggggtgtc ccttcgaggg tcgttagcga gcctccgctt    13080
tcccacgatc tgtcctccga ttcttgttaa ctctagactt tctgatgttc cataccccc     13140 cacgtctcgg caggtgtttc cacaccggta gccagctgtg ccctgaggtg aagaggacc     13200 ggccacccag gaattttcca gtaacgact  cggagtctcc gggattccta tctcccggcc    13260
cccgaatttc                                                           13270
```

<210> SEQ ID NO 2
<211> LENGTH: 2051
<212> TYPE: DNA
<213> ORGANISM: Homo sapiens

<400> SEQUENCE: 2

```
agatcagctg atgccggagg gtttgaagcc gcgccgcgag ggagcgaggt cgcagtgaca      60
gcggcgggcg atcggaccca ggctgccccg ccgtacccgc ctgcgtcccg cgctcccgcc     120
ccagcatgac agccccggcg ggtccgcgcg gctcagagac cgagcggctt ctgaccccca     180
accccgggta tgggacccag gcggggcctt caccggcccc tccgacaccc ccagaagagg     240
aagaccttcg ccgtcgtctc aaatactttt tcatgagtcc ctgcgacaag tttcgagcca     300
agggccgcaa gccctgcaag ctgatgctgc aagtggtcaa gatcctggtg gtcacggtgc     360
agctcatcct gtttgggctc agtaatcagc tggctgtgac attccgggaa gagaacacca     420
tcgccttccg cacacctctt ctgctgggct actcggacgg agcggatgac accttcgcag     480
cctacacgcg ggagcagctg taccaggcca tcttccatgc tgtggaccag tacctggcgt     540
tgcctgacgt gtcactgggc cggtatgcgt atgtccgtgg tgggggtgac ccttggacca     600
atggctcagg gcttgctctc tgccagcggt actaccaccg aggccacgtg gacccggcca     660
acgacacatt tgacattgat ccgatggtgg ttactgactg catccaggtg gatccccccg     720
agcggccccc tccgccccc  agcgacgatc tcaccctctt ggaaagcagc tccagttaca     780
agaacctcac gctcaaattc cacaagctgg tcaatgtcac catccacttc cggctgaaga     840
ccattaacct ccagagcctc atcaataatg agatcccgga ctgctatacc ttcagcgtcc     900
tgatcacgtt tgcaacaaa  gcacacagtg ggcggatccc catcagcctg agacccagg     960 cccacatcca ggagtgtaag cacccagtg  tcttccagca cggagacaac agcttccggc    1020
tcctgtttga cgtggtggtc atcctccacct gctccctgtc cttcctcctc tgcgcccgct    1080
cactccttcg aggcttcctg ctgcagaacg agtttgtggg gttcatgtgg cggcagcggg    1140
```

-continued

```
gacgggtcat cagcctgtgg gagcggctgg aatttgtcaa tggctggtac atcctgctcg    1200
tcaccagcga tgtgctcacc atctcgggca ccatcatgaa gatcggcatc gaggccaaga    1260
acttggcgag ctacgacgtc tgcagcatcc tcctgggcac ctcgacgctg ctggtgtggg    1320
tgggcgtgat ccgctacctg accttcttcc acaactacaa tatcctcatc gccacactgc    1380
gggtggccct gcccagcgtc atgcgcttct gctgctgcgt ggctgtcatc tacctgggct    1440
actgcttctg tggctggatc gtgctggggc cctatcatgt gaagttccgc tcactctcca    1500
tggtgtctga gtgcctgttc tcgctcatca atggggacga catgtttgtg acgttcgccg    1560
ccatgcaggc gcagcagggc cgcagcagcc tggtgtggct cttctcccag ctctaccttt    1620
actccttcat cagcctcttc atctacatgg tgctcagcct cttcatcgcg ctcatcaccg    1680
gcgcctacga caccatcaag catcccggcg gcgcaggcgc agaggagagc gagctgcagg    1740
cctacatcgc acagtgccag gacagcccca cctccggcaa gttccgccgc gggagcggct    1800
cggcctgcag ccttctctgc tgctgcggaa gggacccctc ggaggagcat cgctgctgg    1860 tgaattgatt cgacctgact gccgttggac cgtaggccct ggactgcaga gaccccgcc    1920 cccgaccccg cttatttatt tgtagggttt gcttttaagg atcggctccc tgtcgcgccc    1980
gaggagggcc tggaccttc gtgtcggacc cttggggcg gggagactgg gtggggaggg    2040
tgttgaataa a                                                         2051
```

<210> SEQ ID NO 3
<211> LENGTH: 580
<212> TYPE: PRT
<213> ORGANISM: Homo sapiens

<400> SEQUENCE: 3

```
Met Thr Ala Pro Ala Gly Pro Arg Gly Ser Glu Thr Glu Arg Leu Leu
1               5                   10                  15

Thr Pro Asn Pro Gly Tyr Gly Thr Gln Ala Gly Pro Ser Pro Ala Pro
            20                  25                  30

Pro Thr Pro Pro Glu Glu Glu Asp Leu Arg Arg Arg Leu Lys Tyr Phe
        35                  40                  45

Phe Met Ser Pro Cys Asp Lys Phe Arg Ala Lys Gly Arg Lys Pro Cys
    50                  55                  60

Lys Leu Met Leu Gln Val Val Lys Ile Leu Val Val Thr Val Gln Leu
65                  70                  75                  80

Ile Leu Phe Gly Leu Ser Asn Gln Leu Ala Val Thr Phe Arg Glu Glu
                85                  90                  95

Asn Thr Ile Ala Phe Arg His Leu Phe Leu Leu Gly Tyr Ser Asp Gly
            100                 105                 110

Ala Asp Asp Thr Phe Ala Ala Tyr Thr Arg Glu Gln Leu Tyr Gln Ala
        115                 120                 125

Ile Phe His Ala Val Asp Gln Tyr Leu Ala Leu Pro Asp Val Ser Leu
    130                 135                 140

Gly Arg Tyr Ala Tyr Val Arg Gly Gly Gly Asp Pro Trp Thr Asn Gly
145                 150                 155                 160

Ser Gly Leu Ala Leu Cys Gln Arg Tyr Tyr His Arg Gly His Val Asp
                165                 170                 175

Pro Ala Asn Asp Thr Phe Asp Ile Asp Pro Met Val Val Thr Asp Cys
            180                 185                 190

Ile Gln Val Asp Pro Pro Glu Arg Pro Pro Pro Pro Ser Asp Asp
    195                 200                 205
```

Leu Thr Leu Leu Glu Ser Ser Ser Tyr Lys Asn Leu Thr Leu Lys
    210                 215                 220

Phe His Lys Leu Val Asn Val Thr Ile His Phe Arg Leu Lys Thr Ile
225                 230                 235                 240

Asn Leu Gln Ser Leu Ile Asn Glu Ile Pro Asp Cys Tyr Thr Phe
            245                 250                 255

Ser Val Leu Ile Thr Phe Asp Asn Lys Ala His Ser Gly Arg Ile Pro
    260                 265                 270

Ile Ser Leu Glu Thr Gln Ala His Ile Gln Glu Cys Lys His Pro Ser
    275                 280                 285

Val Phe Gln His Gly Asp Asn Ser Phe Arg Leu Leu Phe Asp Val Val
290                 295                 300

Val Ile Leu Thr Cys Ser Leu Ser Phe Leu Cys Ala Arg Ser Leu
305                 310                 315                 320

Leu Arg Gly Phe Leu Leu Gln Asn Glu Phe Val Gly Phe Met Trp Arg
            325                 330                 335

Gln Arg Gly Arg Val Ile Ser Leu Trp Glu Arg Leu Glu Phe Val Asn
                340                 345                 350

Gly Trp Tyr Ile Leu Leu Val Thr Ser Asp Val Leu Thr Ile Ser Gly
        355                 360                 365

Thr Ile Met Lys Ile Gly Ile Glu Ala Lys Asn Leu Ala Ser Tyr Asp
370                 375                 380

Val Cys Ser Ile Leu Leu Gly Thr Ser Thr Leu Leu Val Trp Val Gly
385                 390                 395                 400

Val Ile Arg Tyr Leu Thr Phe Phe His Asn Tyr Asn Ile Leu Ile Ala
                405                 410                 415

Thr Leu Arg Val Ala Leu Pro Ser Val Met Arg Phe Cys Cys Cys Val
            420                 425                 430

Ala Val Ile Tyr Leu Gly Tyr Cys Phe Cys Gly Trp Ile Val Leu Gly
        435                 440                 445

Pro Tyr His Val Lys Phe Arg Ser Leu Ser Met Val Ser Glu Cys Leu
    450                 455                 460

Phe Ser Leu Ile Asn Gly Asp Asp Met Phe Val Thr Phe Ala Ala Met
465                 470                 475                 480

Gln Ala Gln Gln Gly Arg Ser Ser Leu Val Trp Leu Phe Ser Gln Leu
                485                 490                 495

Tyr Leu Tyr Ser Phe Ile Ser Leu Phe Ile Tyr Met Val Leu Ser Leu
            500                 505                 510

Phe Ile Ala Leu Ile Thr Gly Ala Tyr Asp Thr Ile Lys His Pro Gly
    515                 520                 525

Gly Ala Gly Ala Glu Glu Ser Glu Leu Gln Ala Tyr Ile Ala Gln Cys
530                 535                 540

Gln Asp Ser Pro Thr Ser Gly Lys Phe Arg Arg Gly Ser Gly Ser Ala
545                 550                 555                 560

Cys Ser Leu Leu Cys Cys Cys Gly Arg Asp Pro Ser Glu Glu His Ser
            565                 570                 575

Leu Leu Val Asn
            580

<210> SEQ ID NO 4
<211> LENGTH: 553
<212> TYPE: PRT
<213> ORGANISM: Homo sapiens

<400> SEQUENCE: 4

```
Met Ala Asp Pro Glu Val Val Cys Ser Cys Ser His Glu Glu
 1               5                  10                 15

Glu Asn Arg Cys Asn Phe Asn Gln Gln Thr Ser Pro Ser Glu Glu Leu
            20              25              30

Leu Leu Glu Asp Gln Met Arg Arg Lys Leu Lys Phe Phe Phe Met Asn
        35              40              45

Pro Cys Glu Lys Phe Trp Ala Arg Gly Lys Pro Trp Lys Leu Ala
    50              55              60

Ile Gln Ile Leu Lys Ile Ala Met Val Thr Ile Gln Leu Val Leu Phe
65              70              75                      80

Gly Leu Ser Asn Gln Met Val Val Ala Phe Lys Glu Glu Asn Thr Ile
                85              90              95

Ala Phe Lys His Leu Phe Leu Lys Gly Tyr Met Asp Arg Met Asp Asp
            100             105             110

Thr Tyr Ala Val Tyr Thr Gln Ser Asp Val Tyr Asp Gln Leu Ile Phe
        115             120             125

Ala Val Asn Gln Tyr Leu Gln Leu Tyr Asn Val Ser Val Gly Asn His
130             135             140

Ala Tyr Glu Asn Lys Gly Thr Lys Gln Ser Ala Met Ala Ile Cys Gln
145             150             155             160

His Phe Tyr Lys Arg Gly Asn Ile Tyr Pro Gly Asn Asp Thr Phe Asp
                165             170             175

Ile Asp Pro Glu Ile Glu Thr Glu Cys Phe Phe Val Glu Pro Asp Glu
            180             185             190

Pro Phe His Ile Gly Thr Pro Ala Glu Asn Lys Leu Asn Leu Thr Leu
            195             200             205

Asp Phe His Arg Leu Leu Thr Val Glu Leu Gln Phe Lys Leu Lys Ala
        210             215             220

Ile Asn Leu Gln Thr Val Arg His Gln Glu Leu Pro Asp Cys Tyr Asp
225             230             235             240

Phe Thr Leu Thr Ile Thr Phe Asp Asn Lys Ala His Ser Gly Arg Ile
                245             250             255

Lys Ile Ser Leu Asp Asn Asp Ile Ser Ile Arg Glu Cys Lys Asp Trp
            260             265             270

His Val Ser Gly Ser Ile Gln Lys Asn Thr His Tyr Met Met Ile Phe
            275             280             285

Asp Ala Phe Val Ile Leu Thr Cys Leu Val Ser Leu Ile Leu Cys Ile
        290             295             300

Arg Ser Val Ile Arg Gly Leu Gln Leu Gln Gln Glu Phe Val Asn Phe
305             310             315             320

Phe Leu Leu His Tyr Lys Lys Glu Val Ser Val Ser Asp Gln Met Glu
                325             330             335

Phe Val Asn Gly Trp Tyr Ile Met Ile Ile Ser Asp Ile Leu Thr
            340             345             350

Ile Ile Gly Ser Ile Leu Lys Met Glu Ile Gln Ala Lys Ser Leu Thr
        355             360             365

Ser Tyr Asp Val Cys Ser Ile Leu Leu Gly Thr Ser Thr Met Leu Val
    370             375             380

Trp Leu Gly Val Ile Arg Tyr Leu Gly Phe Phe Ala Lys Tyr Asn Leu
385             390             395             400

Leu Ile Leu Thr Leu Gln Ala Ala Leu Pro Asn Val Ile Arg Phe Cys
                405             410             415
```

```
Cys Cys Ala Ala Met Ile Tyr Leu Gly Tyr Cys Phe Cys Gly Trp Ile
            420                 425                 430

Val Leu Gly Pro Tyr His Asp Lys Phe Arg Ser Leu Asn Met Val Ser
            435                 440                 445

Glu Cys Leu Phe Ser Leu Ile Asn Gly Asp Asp Met Phe Ala Thr Phe
            450                 455                 460

Ala Lys Met Gln Gln Lys Ser Tyr Leu Val Trp Leu Phe Ser Arg Ile
465                 470                 475                 480

Tyr Leu Tyr Ser Phe Ile Ser Leu Phe Ile Tyr Met Ile Leu Ser Leu
            485                 490                 495

Phe Ile Ala Leu Ile Thr Asp Thr Tyr Glu Thr Ile Lys Gln Tyr Gln
            500                 505                 510

Gln Asp Gly Phe Pro Glu Thr Glu Leu Arg Thr Phe Ile Ser Glu Cys
            515                 520                 525

Lys Asp Leu Pro Asn Ser Gly Lys Tyr Arg Leu Glu Asp Asp Pro Pro
530                 535                 540

Val Ser Leu Phe Cys Cys Cys Lys Lys
545                 550
```

```
<210> SEQ ID NO 5
<211> LENGTH: 652
<212> TYPE: PRT
<213> ORGANISM: Drosophila

<400> SEQUENCE: 5

Met Gln Ser Tyr Gly Pro Gly Ala Gln Thr Pro Ala Val Lys Arg
1               5                   10                  15

Arg Thr Asp Ser Tyr Glu Ala Ala Gln Gln Gln Gln Ser Pro Glu
            20                  25                  30

Ser Asp Glu Glu Tyr Val Asn Thr Arg Ile Leu Arg Arg Gln Val Gln
            35                  40                  45

Leu Gln Ser Thr Pro Val Ala Pro Val Pro Met Pro Ile Ser Ala
50                  55                  60

Gly Ser Gly Thr Ala Pro Pro Ser Val Asp Gly Arg Glu Glu Gln Pro
65                  70                  75                  80

Glu Phe Pro Gly Ser Ser Ala Ala Ser Tyr Gln Glu Glu Arg Met Arg
            85                  90                  95

Arg Lys Leu Gln Phe Phe Met Asn Pro Ile Glu Lys Trp Gln Ala
            100                 105                 110

Lys Arg Lys Phe Pro Tyr Lys Phe Val Gln Ile Val Lys Ile Phe
            115                 120                 125

Leu Val Thr Met Gln Leu Cys Leu Phe Ala His Ser Arg Tyr Asn His
            130                 135                 140

Ile Asn Tyr Thr Gly Asp Asn Arg Phe Ala Phe Ser His Leu Phe Leu
145                 150                 155                 160

Arg Gly Trp Asp Ser Ser Arg Glu Val Glu Ser Tyr Pro Pro Ala Val
            165                 170                 175

Gly Pro Phe Ala Leu Tyr Leu Lys Ser Glu Phe Phe Asp Thr Val Gln
            180                 185                 190

Tyr Ala Val Asn Gly Tyr Ala Asn Val Ser Arg Ser Ile Gly Pro Tyr
            195                 200                 205

Asp Tyr Pro Thr Pro Asn Asn Thr Met Pro Pro Leu Lys Leu Cys Leu
            210                 215                 220

Gln Asn Tyr Arg Glu Gly Thr Ile Phe Gly Phe Asn Glu Ser Tyr Ile
225                 230                 235                 240
```

```
Phe Asp Pro His Ile Asp Glu Val Cys Glu Arg Leu Pro Pro Asn Val
            245                 250                 255

Thr Thr Ile Gly Val Glu Asn Tyr Leu Arg Gln Arg Asp Val Glu Val
            260                 265                 270

Asn Phe Ala Ser Leu Val Ser Ala Gln Leu Thr Phe Lys Ile Lys Thr
            275                 280                 285

Val Asn Phe Lys Ala Asn Gly Gly Pro Leu Ser Ala Pro Asp Cys Phe
290                 295                 300

Arg Phe Asp Ile Ser Ile Thr Phe Asn Asn Arg Asp His Asp Gly Gln
305                 310                 315                 320

Met Leu Leu Ser Leu Asp Ala Glu Ala Thr Arg Leu Lys Cys His Gly
                325                 330                 335

Ala Thr Asp Phe Ile Ser Asp Ala Asn Phe Asp Ser Met Leu Arg Ser
                340                 345                 350

Val Leu Asn Ile Phe Val Leu Leu Thr Cys Ala Leu Ser Phe Ala Leu
                355                 360                 365

Cys Thr Arg Ala Leu Trp Arg Ala Tyr Leu Leu Arg Cys Thr Thr Val
370                 375                 380

Asn Phe Phe Arg Ser Gln Phe Gly Lys Glu Leu Ser Phe Asp Gly Arg
385                 390                 395                 400

Leu Glu Phe Val Asn Phe Trp Tyr Ile Met Ile Phe Asn Asp Val
                405                 410                 415

Leu Leu Ile Ile Gly Ser Ala Leu Lys Glu Gln Ile Glu Gly Arg Tyr
                420                 425                 430

Leu Val Val Asp Gln Trp Asp Thr Cys Ser Leu Phe Leu Gly Ile Gly
                435                 440                 445

Asn Leu Leu Val Trp Phe Gly Val Leu Arg Tyr Leu Gly Phe Phe Lys
                450                 455                 460

Thr Tyr Asn Val Val Ile Leu Thr Leu Lys Lys Ala Ala Pro Lys Ile
465                 470                 475                 480

Leu Arg Phe Leu Ile Ala Ala Leu Leu Ile Tyr Ala Gly Phe Val Phe
                485                 490                 495

Cys Gly Trp Leu Ile Leu Gly Pro Tyr His Met Lys Phe Arg Ser Leu
                500                 505                 510

Ala Thr Thr Ser Glu Cys Leu Phe Ala Leu Ile Asn Gly Asp Asp Met
                515                 520                 525

Phe Ala Thr Phe Ala Thr Leu Ser Ser Lys Ala Thr Trp Leu Trp Trp
                530                 535                 540

Phe Cys Gln Ile Tyr Leu Tyr Ser Phe Ile Ser Leu Tyr Ile Tyr Val
545                 550                 555                 560

Val Leu Ser Leu Phe Ile Ala Val Ile Met Asp Ala Tyr Asp Thr Ile
                565                 570                 575

Lys Ala Tyr Tyr Lys Asp Gly Phe Pro Thr Thr Asp Leu Lys Ala Phe
                580                 585                 590

Val Gly Thr Arg Thr Ala Glu Asp Ile Ser Ser Gly Val Phe Met Thr
                595                 600                 605

Asp Leu Asp Asp Phe Asp Gln Thr Ser Phe Leu Asp Val Val Lys Ser
                610                 615                 620

Ile Cys Cys Cys Gly Arg Cys Gly Arg His Gln Glu Pro Ala Gln Pro
625                 630                 635                 640

Asn Ser Gly Tyr Thr Ser Leu Ser Ser Ile Met Lys
                645                 650
```

```
<210> SEQ ID NO 6
<211> LENGTH: 26
<212> TYPE: DNA
<213> ORGANISM: Artificial Sequence
<220> FEATURE:
<223> OTHER INFORMATION: PCR primer

<400> SEQUENCE: 6
cgagggagcg aggtcgcagt gacagc                                        26

<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7
aacaccctcc ccacccagtc tcccc                                         25

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
caacctctac tacctctcc c                                              21

<210> SEQ ID NO 9
<211> LENGTH: 18
<212> TYPE: DNA
<213> ORGANISM: Artificial Sequence
<220> FEATURE:
<223> OTHER INFORMATION: PCR primer

<400> SEQUENCE: 9
aacagtgaag cctcgtcc                                                 18

<210> SEQ ID NO 10
<211> LENGTH: 23
<212> TYPE: DNA
<213> ORGANISM: Artificial Sequence
<220> FEATURE:
<223> OTHER INFORMATION: PCR primer

<400> SEQUENCE: 10
gatataaatg gcaggcagct ttc                                           23

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
ctcaccgtgc tggaagacac                                               20
```